(12) United States Patent
Matsui et al.

(10) Patent No.: US 9,267,124 B2
(45) Date of Patent: Feb. 23, 2016

(54) ALPHA AMYLASE VARIANTS AND POLYNUCLEOTIDES ENCODING SAME

(75) Inventors: Tomoko Matsui, Chiba (JP); Aki Tomiki, Chiba (JP); Guillermo Coward-Kelly, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/131,148

(22) PCT Filed: Jul. 6, 2012

(86) PCT No.: PCT/US2012/045670
§ 371 (c)(1),
(2), (4) Date: Jan. 6, 2014

(87) PCT Pub. No.: WO2013/006756
PCT Pub. Date: Jan. 10, 2013

(65) Prior Publication Data
US 2014/0147893 A1  May 29, 2014

Related U.S. Application Data

(60) Provisional application No. 61/505,192, filed on Jul. 7, 2011, provisional application No. 61/504,771, filed on Jul. 6, 2011.

(51) Int. Cl.
*C12N 9/30* (2006.01)
*C12P 19/20* (2006.01)
*C12P 19/02* (2006.01)
*C12P 19/14* (2006.01)
*C12P 7/06* (2006.01)

(52) U.S. Cl.
CPC . *C12N 9/242* (2013.01); *C12P 7/06* (2013.01); *C12P 19/02* (2013.01); *C12P 19/14* (2013.01); *C12P 19/20* (2013.01); *C07K 2319/20* (2013.01); *Y02E 50/17* (2013.01)

(58) Field of Classification Search
None
See application file for complete search history.

(56) References Cited

FOREIGN PATENT DOCUMENTS

| WO | 90/11352 A1 | 10/1990 |
| WO | 94/02597 A1 | 2/1994 |
| WO | 95/10603 A1 | 4/1995 |
| WO | 95/26397 A1 | 10/1995 |
| WO | 96/23873 A1 | 8/1996 |
| WO | 96/23874 A1 | 8/1996 |
| WO | 2004/055178 A1 | 7/2004 |
| WO | 2006/069290 A2 | 6/2006 |
| WO | 2009/030728 A2 | 3/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — Michael W. Krenicky

(57) ABSTRACT

The present invention relates to variants of alpha amylase. The present invention also relates to polynucleotides encoding the variants; nucleic acid constructs, vectors, and host cells comprising the polynucleotides; and methods of using the variants.

19 Claims, No Drawings

SEQUENCE LISTING

```
<160> NUMBER OF SEQ ID NOS: 48

<210> SEQ ID NO 1
<211> LENGTH: 1416
<212> TYPE: DNA
<213> ORGANISM: Rhizomucor pusillus

<400> SEQUENCE: 1
atgaaattca gcatctctct ctcggcagca attgtactct tcgcggccgc aacaagcctt      60
gcaagccctt tgccccaaca gcagcgatat ggcaaaagag caacttcgga tgactggaaa     120
ggcaaggcca tttatcagct gcttacagat cgatttggcc gcgccgatga ctcaacaagc     180
aactgctcta atttatccaa ctactgtggt ggtacctacg aaggcattac gaagcatctt     240
gactacattt ccggtatggg ctttgatgct atctggatat cgccaattcc caagaactcg     300
gatggaggct accacggcta ctgggctaca gatttctacc aactaaacag caactttggt     360
gatgaatccc agctcaaagc gctcatccag gctgcccatg aacgtgacat gtatgttatg     420
cttgatgtcg tagccaatca tgcaggtccc accagcaatg gctactcggg ttacacattc     480
ggcgatgcaa gtttatatca tcctaaatgc accatagatt acaatgatca gacgtctatt     540
gagcaatgct gggttgctga cgagttgcct gatattgaca ctgaaaattc tgacaacgtg     600
gccattctca acgacatcgt ctccggctgg gtgggtaact atagctttga cggcatccgc     660
attgatactg tcaagcatat tcgcaaggac ttttggacag gctacgcaga agctgccggc     720
gtattcgcaa ctggagaggt cttcaatggt gatccggcct acgttggacc ttatcaaaag     780
tacctgccat ctctcatcaa ttacccaatg tattacgctt tgaacgacgt ctttgtatcc     840
aaaagcaaag gattcagccg catcagcgaa atgctaggat caaatcgcaa tgcgtttgag     900
```

```
gataccagcg tacttacaac gtttgtagac aaccatgaca atccgcgctt cttgaacagt    960
caaagcgaca aggctctctt caagaacgct ctcacatacg tactgctagg tgaaggcatc   1020
ccaattgtgt attatggttc tgagcaaggt ttcagcggag gagcggatcc tgctaaccgt   1080
gaagtgctgt ggaccaccaa ttatgataca tccagcgatc tctaccaatt tatcaagaca   1140
gtcaacagtg tccgcatgaa agcaacaag gccgtctaca tggatattta tgttggcgac    1200
aatgcttacg ccttcaagca cggcgatgct ttggttgttc tcaataacta tggatcaggt   1260
tccacaaacc aagtcagctt cagcgttagt ggcaagttcg atagcggcgc aagcctcatg   1320
gatattgtca gtaacattac caccacggtg tcctcggatg aacagtcac tttcaacctt     1380 aaagatggac ttccggctat cttcacctct gcttaa                              1416
```

<210> SEQ ID NO 2
<211> LENGTH: 471
<212> TYPE: PRT
<213> ORGANISM: Rhizomucor pusillus

<400> SEQUENCE: 2

```
Met Lys Phe Ser Ile Ser Leu Ser Ala Ala Ile Val Leu Phe Ala Ala
1               5                   10                  15

Ala Thr Ser Leu Ala Ser Pro Leu Pro Gln Gln Gln Arg Tyr Gly Lys
                20                  25                  30

Arg Ala Thr Ser Asp Asp Trp Lys Gly Lys Ala Ile Tyr Gln Leu Leu
            35                  40                  45

Thr Asp Arg Phe Gly Arg Ala Asp Asp Ser Thr Ser Asn Cys Ser Asn
        50                  55                  60

Leu Ser Asn Tyr Cys Gly Gly Thr Tyr Glu Gly Ile Thr Lys His Leu
65                  70                  75                  80

Asp Tyr Ile Ser Gly Met Gly Phe Asp Ala Ile Trp Ile Ser Pro Ile
                85                  90                  95

Pro Lys Asn Ser Asp Gly Gly Tyr His Gly Tyr Trp Ala Thr Asp Phe
            100                 105                 110

Tyr Gln Leu Asn Ser Asn Phe Gly Asp Glu Ser Gln Leu Lys Ala Leu
        115                 120                 125

Ile Gln Ala Ala His Glu Arg Asp Met Tyr Val Met Leu Asp Val Val
    130                 135                 140

Ala Asn His Ala Gly Pro Thr Ser Asn Gly Tyr Ser Gly Tyr Thr Phe
145                 150                 155                 160

Gly Asp Ala Ser Leu Tyr His Pro Lys Cys Thr Ile Asp Tyr Asn Asp
                165                 170                 175

Gln Thr Ser Ile Glu Gln Cys Trp Val Ala Asp Glu Leu Pro Asp Ile
            180                 185                 190

Asp Thr Glu Asn Ser Asp Asn Val Ala Ile Leu Asn Asp Ile Val Ser
        195                 200                 205

Gly Trp Val Gly Asn Tyr Ser Phe Asp Gly Ile Arg Ile Asp Thr Val
    210                 215                 220

Lys His Ile Arg Lys Asp Phe Trp Thr Gly Tyr Ala Glu Ala Ala Gly
225                 230                 235                 240

Val Phe Ala Thr Gly Glu Val Phe Asn Gly Asp Pro Ala Tyr Val Gly
                245                 250                 255

Pro Tyr Gln Lys Tyr Leu Pro Ser Leu Ile Asn Tyr Pro Met Tyr Tyr
            260                 265                 270

Ala Leu Asn Asp Val Phe Val Ser Lys Ser Lys Gly Phe Ser Arg Ile
        275                 280                 285
```

```
Ser Glu Met Leu Gly Ser Asn Arg Asn Ala Phe Glu Asp Thr Ser Val
    290                 295                 300

Leu Thr Thr Phe Val Asp Asn His Asp Asn Pro Arg Phe Leu Asn Ser
305                 310                 315                 320

Gln Ser Asp Lys Ala Leu Phe Lys Asn Ala Leu Thr Tyr Val Leu Leu
                325                 330                 335

Gly Glu Gly Ile Pro Ile Val Tyr Tyr Gly Ser Glu Gln Gly Phe Ser
            340                 345                 350

Gly Gly Ala Asp Pro Ala Asn Arg Glu Val Leu Trp Thr Thr Asn Tyr
        355                 360                 365

Asp Thr Ser Ser Asp Leu Tyr Gln Phe Ile Lys Thr Val Asn Ser Val
    370                 375                 380

Arg Met Lys Ser Asn Lys Ala Val Tyr Met Asp Ile Tyr Val Gly Asp
385                 390                 395                 400

Asn Ala Tyr Ala Phe Lys His Gly Asp Ala Leu Val Val Leu Asn Asn
                405                 410                 415

Tyr Gly Ser Gly Ser Thr Asn Gln Val Ser Phe Ser Val Ser Gly Lys
            420                 425                 430

Phe Asp Ser Gly Ala Ser Leu Met Asp Ile Val Ser Asn Ile Thr Thr
        435                 440                 445

Thr Val Ser Ser Asp Gly Thr Val Thr Phe Asn Leu Lys Asp Gly Leu
    450                 455                 460

Pro Ala Ile Phe Thr Ser Ala
465                 470

<210> SEQ ID NO 3
<211> LENGTH: 438
<212> TYPE: PRT
<213> ORGANISM: Rhizomucor pusillus

<400> SEQUENCE: 3

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
```

```
                        180                 185                 190
His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
        210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
            245                 250                 255

Glu Met Leu Gly Ser Asn Arg Asn Ala Phe Glu Asp Thr Ser Val Leu
        260                 265                 270

Thr Thr Phe Val Asp Asn His Asp Asn Pro Arg Phe Leu Asn Ser Gln
    275                 280                 285

Ser Asp Lys Ala Leu Phe Lys Asn Ala Leu Thr Tyr Val Leu Leu Gly
        290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
            325                 330                 335

Thr Ser Ser Asp Leu Tyr Gln Phe Ile Lys Thr Val Asn Ser Val Arg
        340                 345                 350

Met Lys Ser Asn Lys Ala Val Tyr Met Asp Ile Tyr Val Gly Asp Asn
    355                 360                 365

Ala Tyr Ala Phe Lys His Gly Asp Ala Leu Val Val Leu Asn Asn Tyr
        370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
        420                 425                 430

Ala Ile Phe Thr Ser Ala
        435

<210> SEQ ID NO 4
<211> LENGTH: 1638
<212> TYPE: DNA
<213> ORGANISM: Artificial
<220> FEATURE:
<223> OTHER INFORMATION: R. pusilus catalytic core + A. rolfsii AMG
      linker and SBD

<400> SEQUENCE: 4
gcaacttcgg atgactggaa aggcaaggcc atttatcagc tgcttacaga tcgatttggc        60
cgcgccgatg actcaacaag caactgctct aatttatcca actactgtgg tggtacctac       120
gaaggcatta cgaagcatct tgactacatt tccggtatgg gctttgatgc atctgtgata       180
tcgccaattc ccaagaactc ggatggaggc taccacggct actgggctac agatttctac       240
caactaaaca gcaactttgg tgatgaatcc cagctcaaag cgctcatcca ggctgcccat       300
gaacgtgaca tgtatgttat gcttgatgtc gtagccaatc atgcaggtcc accagcaat        360 ggctactcgg gttacacatt cggcgatgca agtttatatc atcctaaatg caccatagat       420
tacaatgatc agacgtctat tgagcaatgc tgggttgctg acgagttgcc tgatattgac       480
actgaaaatt ctgacaacgt ggccattctc aacgacatcg tctccggctg ggtgggtaac       540
```

-continued

```
tatagctttg acggcatccg cattgatact gtcaagcata ttcgcaagga cttttggaca      600
ggctacgcag aagctgccgg cgtattcgca actggagagg tcttcaatgg tgatccggcc      660
tacgttggac cttatcaaaa gtacctgcca tctctcatca attacccaat gtattacgct      720
ttgaacgacg tctttgtatc caaaagcaaa ggattcagcc gcatcagcga atgctagga       780
tcaaatcgca atgcgtttga ggataccagc gtacttacaa cgtttgtaga caaccatgac      840
aatccgcgct tcttgaacag tcaaagcgac aaggctctct tcaagaacgc tctcacatac      900
gtactgctag gtgaaggcat cccaattgtg tattatggtt ctgagcaagg tttcagcgga      960
ggagcggatc ctgctaaccg tgaagtgctg tggaccacca attatgatac atccagcgat     1020
ctctaccaat ttatcaagac agtcaacagt gtccgcatga aaagcaacaa ggccgtctac     1080
atggatattt atgttggcga caatgcttac gccttcaagc acggcgatgc tttggttgtt     1140
ctcaataact atggatcagg ttccacaaac caagtcagct tcagcgttag tggcaagttc     1200
gatagcggcg caagcctcat ggatattgtc agtaacatta ccaccacggt gtcctcggat     1260
ggaacagtca ctttcaacct taagatgga cttccggcta tcttcacctc tgctggtgct      1320
acaagcccgg gtggctcctc gggtagtgtc gaggtcactt tcgacgttta cgctaccaca     1380
gtatatggcc agaacatcta tatcaccggt gatgtgagtg agctcggcaa ctggacaccc     1440
gccaatggtg ttgcactctc ttctgctaac tacccccacct ggagtgccac gatcgctctc    1500
cccgctgaca cgacaatcca gtacaagtat gtcaacattg acggcagcac cgtcatctgg     1560
gaggatgcta tcagcaatcg cgagatcacg acgcccgcca gcggcacata caccgaaaaa     1620
gacacttggg atgaatct                                                    1638
```

<210> SEQ ID NO 5
<211> LENGTH: 546
<212> TYPE: PRT
<213> ORGANISM: Artificial
<220> FEATURE:
<223> OTHER INFORMATION: Rhizomucor pusillus GH13 core plus linker and
      SBD from A. rolfsii AMG

<400> SEQUENCE: 5

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
            165                 170                 175

Trp Val Gly Asn Tyr Ser Phe Asp Gly Ile Arg Ile Asp Thr Val Lys
        180                 185                 190

His Ile Arg Lys Asp Phe Trp Thr Gly Tyr Ala Glu Ala Ala Gly Val
    195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Gly Ala Thr Ser Pro Gly Gly Ser Ser Gly
        435                 440                 445

Ser Val Glu Val Thr Phe Asp Val Tyr Ala Thr Thr Val Tyr Gly Gln
    450                 455                 460

Asn Ile Tyr Ile Thr Gly Asp Val Ser Glu Leu Gly Asn Trp Thr Pro
465                 470                 475                 480

Ala Asn Gly Val Ala Leu Ser Ala Asn Tyr Pro Thr Trp Ser Ala
                485                 490                 495

Thr Ile Ala Leu Pro Ala Asp Thr Thr Ile Gln Tyr Lys Tyr Val Asn
            500                 505                 510

Ile Asp Gly Ser Thr Val Ile Trp Glu Asp Ala Ile Ser Asn Arg Glu
        515                 520                 525

Ile Thr Thr Pro Ala Ser Gly Thr Tyr Thr Glu Lys Asp Thr Trp Asp
    530                 535                 540

Glu Ser
545

<210> SEQ ID NO 6
<211> LENGTH: 1749
<212> TYPE: DNA

<213> ORGANISM: Artificial
<220> FEATURE:
<223> OTHER INFORMATION: R. pusilus catalytic core + A. niger AMG linker and SBD

<400> SEQUENCE: 6

```
gcgacgtcgg acgattggaa gggtaaggcc atttaccagt tgctcacgga ccgattcggt      60
cgcgcagatg actcgacctc gaactgttcg aacctctcga actactgtgg tggcacttac     120
gagggcatca ctaaacatct cgactacatc tccggtatgg gcttcgatgc aatttggatt     180
tcgccgatcc ctaagaactc ggacggtgga taccacggtt actgggccac agacttctat     240
cagctcaact cgaacttcgg cgacgagtcg cagttgaaag cgctcatcca ggcggcccat     300
gagcgggaca tgtatgtcat gctcgatgtg gtggcaaacc acgccggccc gacttcgaac     360
ggatactcgg gttacacttt cggtgatgcc tccctctacc atccgaaatg taccatcgat     420
tacaacgatc agacatcgat cgaacagtgt tgggtcgccg atgagttgcc cgatatcgac     480
accgaaaact cggacaacgt cgcaatcctc aacgacatcg tctccggctg ggtgggtaac     540
tactcgttcg atggtattcg gatcgacacc gtcaagcaca tccgcaagga cttctggaca     600
ggttacgccg aagccgcggg tgtgttcgcg accggagagg tgttcaacgg agaccccgca     660
tacgtgggac cctatcagaa atacttgcct tccctcatca actatcccat gtactacgcc     720
ctcaacgacg tcttcgtctc gaagtcgaag ggtttctcca ggatttccga gatgttgggc     780
tcgaaccgta acgccttcga agatacttcc gtcctcacca cgttcgtgga caaccacgac     840
aaccctcgat tcttgaactc ccagtccgac aaagccctct tcaagaacgc gctcacatac     900
gtgttgctcg gcgaaggaat ccccatcgtc tactatggat cggaacaggg cttctcgggc     960
ggtgcagacc ctgccaaccg agaagtcctc tggactacga actacgacac gtcgtcggat    1020
ctctaccagt tcatcaagac cgtcaactcg gtgcgtatga agtcgaacaa ggcggtgtac    1080
atggacattt acgtgggcga taacgcgtat gcattcaagc atggagacgc cttggtggtc    1140
ctcaacaact acggctcggg ttcgaccaac caggtgtcct ctcggtgtc gggaaagttc    1200
gactccggcg cctccctcat ggatatcgtg tccaacatca caactactgt ctcctcggat    1260
ggcacagtca ctttcaactt gaaggatggc ctcccggcga ttttcacctc cgcaactggc    1320
ggcaccacta cgacggctac cccccactggc tccggcagcg tgacctcgac cagcaagacc    1380
accgcgactc cagcaagac cagcaccagt acgtcatcaa cctcctgtac cactcccacc    1440
gccgtggctg tgactttcga tctgacagct accaccacct acggcgagaa catctacctg    1500
gtcggatcga tctctcagct gggtgactgg gaaaccagcg acggcatagc tctgagtgct    1560
gacaagtaca cttccagcga cccgctctgg tatgtcactg tgactctgcc ggctggtgag    1620
tcgtttgagt acaagtttat ccgcattgag agcgatgact ccgtggagtg ggagagtgat    1680
cccaaccgag aatacaccgt tcctcaggcg tgcggaacgt cgaccgcgac ggtgactgac    1740
acctggcgg                                                             1749
```

<210> SEQ ID NO 7
<211> LENGTH: 583
<212> TYPE: PRT
<213> ORGANISM: Artificial
<220> FEATURE:
<223> OTHER INFORMATION: Rhizomucor pusillus GH13 core plus linker and SBD from A. niger AMG

<400> SEQUENCE: 7

Ala Thr Ser Asp Asp Trp Lys Gly Lys Ala Ile Tyr Gln Leu Leu Thr

```
  1               5                   10                  15
Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
                35                  40                  45

Tyr Ile Ser Gly Met Gly Phe Asp Ala Ile Trp Ile Ser Pro Ile Pro
                50                  55                  60

Lys Asn Ser Asp Gly Gly Tyr His Gly Tyr Trp Ala Thr Asp Phe Tyr
 65                 70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Gly
                115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
                195                 200                 205

Phe Ala Thr Gly Glu Val Phe Asn Gly Asp Pro Ala Tyr Val Gly Pro
210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
                260                 265                 270

Thr Thr Phe Val Asp Asn His Asp Asn Pro Arg Phe Leu Asn Ser Gln
                275                 280                 285

Ser Asp Lys Ala Leu Phe Lys Asn Ala Leu Thr Tyr Val Leu Leu Gly
                290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
                340                 345                 350

Met Lys Ser Asn Lys Ala Val Tyr Met Asp Ile Tyr Val Gly Asp Asn
                355                 360                 365

Ala Tyr Ala Phe Lys His Gly Asp Ala Leu Val Val Leu Asn Asn Tyr
                370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
                420                 425                 430
```

```
Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
450                 455                 460

Ser Lys Thr Ser Thr Ser Ser Thr Ser Cys Thr Thr Pro Thr
465                 470                 475                 480

Ala Val Ala Val Thr Phe Asp Leu Thr Ala Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
            530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 8
<211> LENGTH: 6
<212> TYPE: PRT
<213> ORGANISM: Pachykytospora papayracea

<400> SEQUENCE: 8

Gly Asn Ala Gly Pro Ser
1               5

<210> SEQ ID NO 9
<211> LENGTH: 7
<212> TYPE: PRT
<213> ORGANISM: Trametes cingulata

<400> SEQUENCE: 9

Gly Ser Gly Gly Ala Gly Thr
1               5

<210> SEQ ID NO 10
<211> LENGTH: 11
<212> TYPE: PRT
<213> ORGANISM: Leucopaxillus gigantus

<400> SEQUENCE: 10

Gly Gly Gly Ser Asn Pro Gly Gly Gly Gly Ser
1               5                   10

<210> SEQ ID NO 11
<211> LENGTH: 35
<212> TYPE: PRT
<213> ORGANISM: Trichophaea saccata

<400> SEQUENCE: 11

Gly Thr Gly Ser Ser Thr Thr Ser Ser Thr Ser Ala Thr Ser Thr Thr
1               5                   10                  15

Lys Ser Ser Thr Thr Ser Thr Thr Ala Thr Ser Thr Ser Val Ala
            20                  25                  30

Thr Ser Ser
```

```
<210> SEQ ID NO 12
<211> LENGTH: 25
<212> TYPE: PRT
<213> ORGANISM: Subulispora provurvata

<400> SEQUENCE: 12

Gly Gly Ser Gly Thr Thr Thr Thr Thr Thr Ser Thr Ala Gly Thr
1               5                   10                  15

Ser Pro Thr Ser Thr Ala Cys Ser Ser
            20                  25

<210> SEQ ID NO 13
<211> LENGTH: 15
<212> TYPE: PRT
<213> ORGANISM: Valsaria rubricosa

<400> SEQUENCE: 13

Thr Thr Thr Lys Thr Ser Thr Ser Thr Ala Ser Cys Ala Ala Thr
1               5                   10                  15

<210> SEQ ID NO 14
<211> LENGTH: 26
<212> TYPE: PRT
<213> ORGANISM: Acremonium sp

<400> SEQUENCE: 14

Thr Ser Thr Ala Leu Pro Thr Ser Ser Leu Thr Ala Ala Ser Ala Thr
1               5                   10                  15

Thr Thr Ala Ser Ala Cys Ser Leu Ser Ala
            20                  25

<210> SEQ ID NO 15
<211> LENGTH: 15
<212> TYPE: PRT
<213> ORGANISM: Meripilus giganteus

<400> SEQUENCE: 15

Ala Thr Pro Thr Ser Ala Pro Ser Thr Thr Pro Thr Ser Gly Thr
1               5                   10                  15

<210> SEQ ID NO 16
<211> LENGTH: 3
<212> TYPE: PRT
<213> ORGANISM: Bacillus flavothermus

<400> SEQUENCE: 16

Asn Ala Thr
1

<210> SEQ ID NO 17
<211> LENGTH: 62
<212> TYPE: PRT
<213> ORGANISM: Bacillus flavothermus

<400> SEQUENCE: 17

Thr Glu Lys Leu Ala Gly Ser Lys Ile Cys Ser Gly Ser Gly Asn Thr
1               5                   10                  15

Thr Thr Thr Thr Thr Ala Ala Thr Ser Thr Ser Lys Ala Thr Thr Ser
            20                  25                  30

Ser Ser Ser Ser Ser Ala Ala Ala Thr Thr Ser Ser Ser Cys Thr Ala
            35                  40                  45
```

```
Thr Ser Thr Thr Leu Pro Ile Thr Phe Glu Glu Leu Val Thr
        50                  55                  60
```

<210> SEQ ID NO 18
<211> LENGTH: 35
<212> TYPE: PRT
<213> ORGANISM: Bacillus flavothermus

<400> SEQUENCE: 18

```
Thr Glu Lys Leu Ala Gly Ser Lys Ile Cys Ser Thr Tyr Thr Thr Ala
1               5                   10                  15

Ser Pro Pro Gly Gly Cys Ser Ala Gly Thr Val Val Phe Asp Val
            20                  25                  30

Tyr Val Gln
        35
```

<210> SEQ ID NO 19
<211> LENGTH: 11
<212> TYPE: PRT
<213> ORGANISM: Athelia rolfsii

<400> SEQUENCE: 19

```
Gly Ala Thr Ser Pro Gly Gly Ser Ser Gly Ser
1               5                   10
```

<210> SEQ ID NO 20
<211> LENGTH: 31
<212> TYPE: PRT
<213> ORGANISM: Aspergillus kawachii

<400> SEQUENCE: 20

```
Thr Thr Thr Thr Thr Thr Ala Ala Ala Thr Ser Thr Ser Lys Ala Thr
1               5                   10                  15

Thr Ser Ser Ser Ser Ser Ser Ala Ala Ala Thr Thr Ser Ser Ser
            20                  25                  30
```

<210> SEQ ID NO 21
<211> LENGTH: 37
<212> TYPE: PRT
<213> ORGANISM: Aspergillus niger

<400> SEQUENCE: 21

```
Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
            20                  25                  30

Thr Ser Ser Thr Ser
        35
```

<210> SEQ ID NO 22
<211> LENGTH: 32
<212> TYPE: PRT
<213> ORGANISM: Coniochaeta sp

<400> SEQUENCE: 22

```
Thr Thr Thr Thr Ala Thr Thr Lys Thr Ser Thr Thr Leu Thr Thr Ser
1               5                   10                  15

Thr Thr Thr Thr Ser Thr Lys Thr Ser Ser Ser Cys Thr Ala Thr Ala
            20                  25                  30
```

<210> SEQ ID NO 23

```
<211> LENGTH: 41
<212> TYPE: PRT
<213> ORGANISM: Coniochaeta sp

<400> SEQUENCE: 23

Thr Thr Ser Thr Ser Thr Gly Thr Ser Thr Thr Arg Thr Gly Thr
1               5                   10                  15

Thr Leu Thr Thr Ser Thr Lys Thr Thr Ala Ser Thr Thr Thr Lys
            20                  25                  30

Ser Ser Ser Ser Cys Thr Ala Thr Ala
        35                  40

<210> SEQ ID NO 24
<211> LENGTH: 10
<212> TYPE: PRT
<213> ORGANISM: Trametes corrugata

<400> SEQUENCE: 24

Thr Thr Thr Ala Ser Ala Cys Pro Thr Ser
1               5                   10

<210> SEQ ID NO 25
<211> LENGTH: 11
<212> TYPE: PRT
<213> ORGANISM: Valsario spartii

<400> SEQUENCE: 25

Thr Thr Ser Pro Thr Ala Gly Cys Pro Ser Thr
1               5                   10

<210> SEQ ID NO 26
<211> LENGTH: 44
<212> TYPE: PRT
<213> ORGANISM: Penicillium sp

<400> SEQUENCE: 26

Thr Thr Thr Thr Ser Ser Thr Ala Ser Thr Ser Thr Thr Ser Thr
1               5                   10                  15

Thr Leu Lys Thr Thr Thr Thr Thr Ser Thr Thr Ser Lys Thr Thr
            20                  25                  30

Ser Thr Thr Ser Thr Ser Cys Thr Gln Ala Thr Ala
        35                  40

<210> SEQ ID NO 27
<211> LENGTH: 102
<212> TYPE: PRT
<213> ORGANISM: Trichopheraea saccata

<400> SEQUENCE: 27

Gln Asn Thr Lys Arg Ser Thr Gln Val Ser Leu Ile Ser Tyr Thr Phe
1               5                   10                  15

Ser Asn Asn Ile Leu Ser Gly Ser Ile Ser Ile Gln Asn Ile Ala Tyr
            20                  25                  30

Ala Lys Thr Val Ser Val Thr Tyr Ala Ile Gly Ser Ser Trp Ser Ser
        35                  40                  45

Ser Gln Val Ile Ser Ala Ala Tyr Ser Thr Gly Pro Asp Ser Thr Gly
    50                  55                  60

Tyr Glu Val Trp Thr Phe Ser Gly Thr Ala Thr Gly Ala Thr Gln Phe
65                  70                  75                  80

Tyr Ile Ala Tyr Thr Val Ser Gly Thr Ser Tyr Tyr Asp Pro Gly Asn
                85                  90                  95
```

Gly Ile Asn Tyr Thr Ile
            100

<210> SEQ ID NO 28
<211> LENGTH: 94
<212> TYPE: PRT
<213> ORGANISM: Pachykytospora papayracea

<400> SEQUENCE: 28

Val Lys Val Thr Phe Asn Val Gln Ala Thr Thr Thr Phe Gly Glu Asn
1               5                   10                  15

Ile Tyr Ile Thr Gly Asn Thr Ala Ala Leu Gln Asn Trp Ser Pro Asp
            20                  25                  30

Asn Ala Leu Leu Leu Ser Ala Asp Lys Tyr Pro Thr Trp Ser Ile Thr
        35                  40                  45

Leu Asp Leu Pro Ala Asn Thr Val Val Glu Tyr Lys Tyr Ile Arg Lys
    50                  55                  60

Phe Asn Gly Gln Val Thr Trp Glu Ser Asp Pro Asn Asn Ser Ile Thr
65                  70                  75                  80

Thr Pro Ala Asp Gly Thr Phe Thr Gln Asn Asp Thr Trp Arg
                85                  90

<210> SEQ ID NO 29
<211> LENGTH: 94
<212> TYPE: PRT
<213> ORGANISM: Trametes cingulata

<400> SEQUENCE: 29

Val Ala Val Thr Phe Asn Val Gln Ala Thr Thr Val Phe Gly Glu Asn
1               5                   10                  15

Ile Tyr Ile Thr Gly Ser Val Pro Ala Leu Gln Asn Trp Ser Pro Asp
            20                  25                  30

Asn Ala Leu Ile Leu Ser Ala Ala Asn Tyr Pro Thr Trp Ser Ile Thr
        35                  40                  45

Val Asn Leu Pro Ala Ser Thr Thr Ile Glu Tyr Lys Tyr Ile Arg Lys
    50                  55                  60

Phe Asn Gly Ala Val Thr Trp Glu Ser Asp Pro Asn Asn Ser Ile Thr
65                  70                  75                  80

Thr Pro Ala Ser Gly Thr Phe Thr Gln Asn Asp Thr Trp Arg
                85                  90

<210> SEQ ID NO 30
<211> LENGTH: 94
<212> TYPE: PRT
<213> ORGANISM: Leucopaxillus gigantus

<400> SEQUENCE: 30

Val Ser Val Thr Phe Asn Val Gln Ala Thr Thr Thr Phe Gly Glu Asn
1               5                   10                  15

Ile Phe Leu Thr Gly Ser Ile Asn Glu Leu Ala Asn Trp Ser Pro Asp
            20                  25                  30

Asn Ala Leu Ala Leu Ser Ala Ala Asn Tyr Pro Thr Trp Ser Ser Thr
        35                  40                  45

Val Asn Val Pro Ala Ser Thr Thr Ile Gln Tyr Lys Phe Ile Arg Lys
    50                  55                  60

Phe Asn Gly Ala Ile Thr Trp Glu Ser Asp Pro Asn Arg Gln Ile Thr
65                  70                  75                  80

```
Thr Pro Ser Ser Gly Ser Phe Val Gln Asn Asp Ser Trp Lys
                85                  90

<210> SEQ ID NO 31
<211> LENGTH: 101
<212> TYPE: PRT
<213> ORGANISM: Subulispora provurvata

<400> SEQUENCE: 31

Val Pro Val Thr Phe Arg Glu Thr Val Thr Thr Val Gly Gln Thr
1               5                   10                  15

Ile Lys Ile Ser Gly Asp Val Ser Ala Leu Gly Asn Trp Asp Thr Asp
                20                  25                  30

Asp Ala Val Ala Leu Ser Ala Ala Ser Tyr Thr Ser Ser Asn Pro Val
            35                  40                  45

Trp Asp Val Thr Val Ser Phe Ala Pro Gly Thr Val Ile Glu Tyr Lys
        50                  55                  60

Tyr Ile Asn Val Ala Ser Gly Gly Ala Val Thr Trp Glu Ala Asp Pro
65                  70                  75                  80

Asn His Thr Tyr Thr Val Pro Ser Ser Cys Ala Thr Ala Val Val Ser
                85                  90                  95

Asn Thr Trp Gln Thr
            100

<210> SEQ ID NO 32
<211> LENGTH: 100
<212> TYPE: PRT
<213> ORGANISM: Valsaria rubricosa

<400> SEQUENCE: 32

Val Ala Val Thr Phe Asn Glu Leu Val Thr Thr Asn Tyr Gly Asp Thr
1               5                   10                  15

Ile Arg Leu Thr Gly Ser Ile Ser Gln Leu Ser Ser Trp Ser Ala Thr
                20                  25                  30

Ser Gly Leu Ala Leu Ser Ala Ser Ala Tyr Thr Ser Ser Asn Pro Leu
            35                  40                  45

Trp Ser Val Thr Val Ser Leu Pro Ala Gly Thr Ser Phe Glu Tyr Lys
        50                  55                  60

Phe Val Arg Ile Thr Ser Asp Gly Thr Val Thr Trp Glu Ser Asp Pro
65                  70                  75                  80

Asn Arg Ser Tyr Thr Val Pro Thr Cys Ala Ser Thr Ala Thr Ile Ser
                85                  90                  95

Asn Thr Trp Arg
            100

<210> SEQ ID NO 33
<211> LENGTH: 98
<212> TYPE: PRT
<213> ORGANISM: Acremonium sp

<400> SEQUENCE: 33

Val Asn Ile Thr Phe Asn Glu Leu Val Thr Thr Val Trp Gly Asp Thr
1               5                   10                  15

Ile Lys Leu Ala Gly Asn Ile Ser Ala Leu Gly Ser Trp Ser Pro Ser
                20                  25                  30

Ser Ala Leu Thr Leu Ser Ala Ser Gln Tyr Ser Gln Ser Asn Pro Leu
            35                  40                  45

Trp Ser Val Ser Thr Leu Leu Gly Pro Gly Thr Val Ile Glu Tyr Lys
```

```
            50                  55                  60
Phe Ile Lys Val Ser Ala Ser Gly Thr Val Thr Trp Glu Ser Asp Pro
 65                  70                  75                  80

Asn Arg Val Tyr Thr Val Pro Cys Ala Thr Ala Thr Val Ser Ser Thr
                 85                  90                  95

Trp Arg

<210> SEQ ID NO 34
<211> LENGTH: 95
<212> TYPE: PRT
<213> ORGANISM: Meripilus giganteus

<400> SEQUENCE: 34

Val Ser Met Thr Phe Ala Glu Gln Ala Thr Thr Thr Phe Gly Glu Asn
  1               5                  10                  15

Ile Phe Leu Val Gly Ser Ile Ser Gln Leu Gly Asn Trp Asn Pro Ala
                 20                  25                  30

Ser Ala Ile Ala Leu Ser Ser Ala Ala Tyr Pro Thr Trp Ser Val Ser
             35                  40                  45

Val Asn Ile Pro Ala Gly Thr Thr Phe Gln Tyr Lys Phe Ile Arg Lys
 50                  55                  60

Glu Thr Asp Gly Ser Val Val Trp Glu Ser Asp Pro Asn Arg Gln Ala
 65                  70                  75                  80

Thr Ala Pro Ala Ser Gly Thr Thr Thr Leu Thr Ser Ser Trp Arg
                 85                  90                  95

<210> SEQ ID NO 35
<211> LENGTH: 87
<212> TYPE: PRT
<213> ORGANISM: Bacillus flavothermus

<400> SEQUENCE: 35

Thr Val Trp Gly Gln Asn Val Tyr Val Val Gly Asn Ile Ser Gln Leu
  1               5                  10                  15

Gly Asn Trp Asp Pro Val His Ala Val Gln Met Thr Pro Ser Ser Tyr
                 20                  25                  30

Pro Thr Trp Thr Val Thr Ile Pro Leu Leu Gln Gly Gln Asn Ile Gln
             35                  40                  45

Phe Lys Phe Ile Lys Lys Asp Ser Ala Gly Asn Val Ile Trp Glu Asp
 50                  55                  60

Ile Ser Asn Arg Thr Tyr Thr Val Pro Thr Ala Ala Ser Gly Ala Tyr
 65                  70                  75                  80

Thr Ala Ser Trp Asn Val Pro
                 85

<210> SEQ ID NO 36
<211> LENGTH: 97
<212> TYPE: PRT
<213> ORGANISM: Athelia rolfsii

<400> SEQUENCE: 36

Val Glu Val Thr Phe Asp Val Tyr Ala Thr Thr Val Tyr Gly Gln Asn
  1               5                  10                  15

Ile Tyr Ile Thr Gly Asp Val Ser Glu Leu Gly Asn Trp Thr Pro Ala
                 20                  25                  30

Asn Gly Val Ala Leu Ser Ser Ala Asn Tyr Pro Thr Trp Ser Ala Thr
             35                  40                  45
```

```
Ile Ala Leu Pro Ala Asp Thr Thr Ile Gln Tyr Lys Tyr Val Asn Ile
 50                  55                  60

Asp Gly Ser Thr Val Ile Trp Glu Asp Ala Ile Ser Asn Arg Glu Ile
 65                  70                  75                  80

Thr Thr Pro Ala Ser Gly Thr Tyr Thr Glu Lys Asp Thr Trp Asp Glu
                 85                  90                  95

Ser
```

```
<210> SEQ ID NO 37
<211> LENGTH: 109
<212> TYPE: PRT
<213> ORGANISM: Aspergillus kawachii

<400> SEQUENCE: 37

Cys Thr Ala Thr Ser Thr Thr Leu Pro Ile Thr Phe Glu Glu Leu Val
 1               5                  10                  15

Thr Thr Thr Tyr Gly Glu Glu Val Tyr Leu Ser Gly Ser Ile Ser Gln
                 20                  25                  30

Leu Gly Glu Trp Asp Thr Ser Asp Ala Val Lys Leu Ser Ala Asp Asp
             35                  40                  45

Tyr Thr Ser Ser Asn Pro Glu Trp Ser Val Thr Val Ser Leu Pro Val
 50                  55                  60

Gly Thr Thr Phe Glu Tyr Lys Phe Ile Lys Val Asp Glu Gly Gly Ser
 65                  70                  75                  80

Val Thr Trp Glu Ser Asp Pro Asn Arg Glu Tyr Thr Val Pro Glu Cys
                 85                  90                  95

Gly Asn Gly Ser Gly Glu Thr Val Val Asp Thr Trp Arg
                100                 105
```

```
<210> SEQ ID NO 38
<211> LENGTH: 108
<212> TYPE: PRT
<213> ORGANISM: Aspergillus niger

<400> SEQUENCE: 38

Cys Thr Thr Pro Thr Ala Val Ala Val Thr Phe Asp Leu Thr Ala Thr
 1               5                  10                  15

Thr Thr Tyr Gly Glu Asn Ile Tyr Leu Val Gly Ser Ile Ser Gln Leu
                 20                  25                  30

Gly Asp Trp Glu Thr Ser Asp Gly Ile Ala Leu Ser Ala Asp Lys Tyr
             35                  40                  45

Thr Ser Ser Asp Pro Leu Trp Tyr Val Thr Val Thr Leu Pro Ala Gly
 50                  55                  60

Glu Ser Phe Glu Tyr Lys Phe Ile Arg Ile Glu Ser Asp Asp Ser Val
 65                  70                  75                  80

Glu Trp Glu Ser Asp Pro Asn Arg Glu Tyr Thr Val Pro Gln Ala Cys
                 85                  90                  95

Gly Thr Ser Thr Ala Thr Val Thr Asp Thr Trp Arg
                100                 105
```

```
<210> SEQ ID NO 39
<211> LENGTH: 99
<212> TYPE: PRT
<213> ORGANISM: Coniochaeta sp

<400> SEQUENCE: 39

Val Ala Ile Thr Phe Asn Glu Leu Val Ser Thr Ser Tyr Gly Asp Thr
 1               5                  10                  15
```

```
Val Lys Leu Thr Gly Asn Ile Thr Ala Leu Gly Ser Trp Asn Thr Ala
            20                  25                  30

Asn Ala Val Ser Leu Ser Ala Ser Gln Tyr Thr Ser Gly Ser Pro Leu
            35                  40                  45

Trp Ser Gly Thr Val Ser Leu Pro Pro Gly Val Gly Val Gln Tyr Lys
 50                  55                  60

Phe Val Arg Val Gly Ser Ser Gly Ser Val Thr Trp Glu Ala Asp Pro
 65                  70                  75                  80

Asn His Thr Tyr Ser Val Pro Cys Ala Ala Ala Thr Val Gly Gly Ser
                85                  90                  95

Trp Gln Ser
```

<210> SEQ ID NO 40
<211> LENGTH: 128
<212> TYPE: PRT
<213> ORGANISM: Zea mays

<400> SEQUENCE: 40

```
Val Arg Val Arg Phe Val Leu Lys Arg Gln Cys Thr Phe Gly Gln Ser
 1               5                  10                  15

Val Cys Leu Val Gly Asp Asp Pro Ala Leu Gly Leu Trp Asp Leu Ser
            20                  25                  30

Asn Ala Phe Pro Leu Lys Trp Ala Glu Ser His Asp Trp Thr Leu Glu
            35                  40                  45

Lys Asp Leu Pro Ala Asn Lys Leu Ile Glu Phe Lys Phe Leu Leu Gln
 50                  55                  60

Asp Ser Thr Gly Lys Leu His Trp Gln Gly Gly Pro Asn Arg Ser Phe
 65                  70                  75                  80

Gln Thr Gly Glu Thr Ala Ala Asn Thr Leu Val Val Phe Glu Asp Trp
                85                  90                  95

Gly Asp Val Lys Asn Gln Lys Ile Val Glu Glu Gly Val Ala Ser
            100                 105                 110

Ala Gly Ile Glu Gln Thr Val Val Ser Asn Asp Ser Glu Ser Arg Lys
            115                 120                 125
```

<210> SEQ ID NO 41
<211> LENGTH: 99
<212> TYPE: PRT
<213> ORGANISM: Coniochaeta sp

<400> SEQUENCE: 41

```
Val Ala Ile Thr Phe Asn Glu Leu Val Ser Thr Ala Tyr Gly Asp Thr
 1               5                  10                  15

Ile Lys Leu Ser Gly Asn Ile Thr Ala Leu Gly Ser Trp Asn Ala Ala
            20                  25                  30

Asn Ala Val Ser Leu Ser Ala Ser Gly Tyr Thr Ala Ala Asn Pro Leu
            35                  40                  45

Trp Ser Gly Thr Val Asn Leu Ala Pro Gly Thr Val Gln Tyr Lys
 50                  55                  60

Phe Val Lys Val Gly Ser Ser Gly Ser Val Thr Trp Glu Ala Asp Pro
 65                  70                  75                  80

Asn His Thr Tyr Ala Val Pro Cys Ala Gly Ala Thr Val Ser Gly Ser
                85                  90                  95

Trp Gln Ser
```

```
<210> SEQ ID NO 42
<211> LENGTH: 100
<212> TYPE: PRT
<213> ORGANISM: Trametes corrugata

<400> SEQUENCE: 42

Val Ala Val Ser Phe Thr His Ser Ile Thr Thr Val Pro Gly Asp Thr
1               5                   10                  15

Ile Lys Ile Ala Gly Asn Thr Thr Gln Leu Gly Ser Trp Thr Val Ala
            20                  25                  30

Ser Ala Pro Ala Leu Ser Ala Ser Ser Tyr Thr Ser Ser Asn Pro Val
        35                  40                  45

Trp Thr Ile Thr Leu Ser Met Pro Ala Lys Gln Ala Val Gln Tyr Lys
    50                  55                  60

Phe Val Lys Val Ala Ser Gly Gly Ala Val Thr Trp Glu Ser Asp Pro
65                  70                  75                  80

Asn Arg Ser Tyr Ser Val Pro Ala Cys Gln Ala Ser Ala Ala Val Ser
                85                  90                  95

Ser Ser Trp Gln
            100

<210> SEQ ID NO 43
<211> LENGTH: 101
<212> TYPE: PRT
<213> ORGANISM: Valsario spartii

<400> SEQUENCE: 43

Val Ser Val Thr Phe Thr Asn Leu Val Thr Gln Val Gly Asp Thr
1               5                   10                  15

Ile Lys Val Thr Gly Asn Val Ser Gln Leu Gly Asn Trp Asn Pro Ser
            20                  25                  30

Ser Ala Pro Ala Leu Ser Ala Thr Gly Tyr Thr Ala Ser Asn Pro Lys
        35                  40                  45

Trp Ser Gly Thr Val Lys Leu Pro Ala Gly Ser Thr Val Gln Tyr Lys
    50                  55                  60

Phe Val Lys Val Ala Ser Gly Gly Gly Ala Val Thr Trp Glu Ser Asp
65                  70                  75                  80

Pro Asn Arg Ser Tyr Ser Val Pro Ser Cys Gln Ala Ser Ala Thr Val
                85                  90                  95

Asp Ser Ser Trp Lys
            100

<210> SEQ ID NO 44
<211> LENGTH: 103
<212> TYPE: PRT
<213> ORGANISM: Penicillium sp

<400> SEQUENCE: 44

Leu Pro Val Leu Phe Lys Glu Ile Val Thr Thr Ser Tyr Gly Gln Ser
1               5                   10                  15

Ile Tyr Ile Ser Gly Ser Ile Ser Gln Leu Gly Ser Trp Asp Thr Ser
            20                  25                  30

Ser Ala Val Ala Leu Ser Ala Asp Gln Tyr Thr Ser Ser His Leu
        35                  40                  45

Trp Tyr Val Val Val Thr Ile Pro Val Gly Thr Ser Phe Gln Tyr Lys
    50                  55                  60

Phe Ile Glu Glu Thr Ser Gly Ser Ser Thr Ile Thr Trp Glu Ser Asp
65                  70                  75                  80
```

```
Pro Asn Arg Ser Tyr Thr Val Pro Thr Gly Cys Ala Gly Ser Thr Ala
                85                  90                  95

Thr Val Thr Ala Thr Trp Arg
            100

<210> SEQ ID NO 45
<211> LENGTH: 20
<212> TYPE: DNA
<213> ORGANISM: Artificial
<220> FEATURE:
<223> OTHER INFORMATION: PCR primer

<400> SEQUENCE: 45
taggagttta gtgaacttgc                                             20

<210> SEQ ID NO 46
<211> LENGTH: 18
<212> TYPE: DNA
<213> ORGANISM: Artificial
<220> FEATURE:
<223> OTHER INFORMATION: PCR primer

<400> SEQUENCE: 46
ttcgagcgtc ccaaaacc                                               18

<210> SEQ ID NO 47
<211> LENGTH: 38
<212> TYPE: DNA
<213> ORGANISM: Artificial
<220> FEATURE:
<223> OTHER INFORMATION: PCR primer

<400> SEQUENCE: 47
cggctatctt cacctctgct actggcggca ccactacg                         38

<210> SEQ ID NO 48
<211> LENGTH: 47
<212> TYPE: DNA
<213> ORGANISM: Artificial
<220> FEATURE:
<223> OTHER INFORMATION: PCR primer

<400> SEQUENCE: 48
ctaattacat gatgcggccc gcggccgcct accgccaggt gtcagtc                47
```

ALPHA AMYLASE VARIANTS AND POLYNUCLEOTIDES ENCODING SAME

CROSS-REFERENCE TO RELATED APPLICATIONS

This application is a 35 U.S.C. 371 national application of PCT/US2012/045670 filed Jul. 6, 2012, which claims priority or the benefit under 35 U.S.C. 119 of U.S. provisional application Nos. 61/504,771 and 61/505,192 filed Jul. 6, 2011 and Jul. 7, 2011, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to variants of an alpha amylase, polynucleotides encoding the variants, methods of producing the variants, and methods of using the variants.

2. Description of the Related Art

The present invention provides variants of a parent alpha amylase with improved properties compared to its parent. Alpha-amylases (1,4-α-D-glucan glucanohydrolase, EC 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of alpha-amylases referred to as "Termamyl®-like alpha-amylases" and variants thereof are known from, e.g., WO 90/11352, WO 95/10603, WO 95/26397, WO 96/23873 and WO 96/23874. Termamyl®-like alpha-amylases are very thermostable and therefore suitable for processes carried out at high temperatures such as starch liquefaction in dextrose production processes.

Another group of alpha-amylases are referred to as "Fungamyl™-like alpha-amylases", which are alpha-amylases related or homologous to the alpha-amylase derived from *Aspergillus oryzae*. The Fungamyl-like alpha-amylases have a relatively low thermostability e.g. the commercial product sold under the tradename FUNGAMYL™ by Novozymes A/S, Denmark, has an optimum around 55° C., and is not suitable for processes carried out at high temperatures. Fungamyl™-like alpha-amylases are today used for making syrups for, e.g., the brewing industry.

An alpha-amylase with increased thermostability, preferably at an acidic pH, has previously been successfully isolated. WO 2004/055178 discloses a gene from *Rhizomucor pusillus* encoding an alpha-amylase denoted AM782. Characterization of this amylase has shown it to be a highly thermoacidophilic alpha-amylase which has a highly interesting activity as demonstrated by the sugar profile from maltodextrin hydrolysis by amylase AM782. The amylase AM782 can work at a very high temperature, at least up to 70° C. However, this alpha amylase has poor storage stability if stored without cooling. It is an object of the present invention to provide storage stable variants of AM782 as SEQ ID NO: 3 (mature polypeptide), which have retained good raw starch hydrolysis activity.

SUMMARY OF THE INVENTION

The present invention relates to alpha amylase variants, comprising a substitution, at one or more positions corresponding to positions 128, 143, 141, 192, 20, 76, 123, 136, 142, 165, 219, 224, 265, 383, and 410 of the mature polypeptide of SEQ ID NO: 2, wherein the variant has alpha amylase activity.

The present invention also relates to isolated polynucleotides encoding the variants; nucleic acid constructs, vectors, and host cells comprising the polynucleotides; and methods of producing the variants.

The present invention also relates to methods of producing a fermentation product from starch-containing material using the variants of the invention.

DETAILED DESCRIPTION OF THE INVENTION

The present invention relates to variants of a parent alpha amylase, comprising a substitution at one or more (several) positions corresponding to positions 128, 143, 141, 192, 20, 76, 123, 136, 142, 165, 219, 224, 265, 383, and 410 of the mature polypeptide of SEQ ID NO: 2, wherein the variant has alpha amylase activity.

DEFINITIONS

Alpha amylase activity: The term "alpha amylase activity" means an 1,4-alpha-D-glucan glucanohydrolase, EC. 3.2.1.1, which catalyze hydrolysis of starch and other linear and branched 1,4-glucosidic oligo- and polysaccharides. For purposes of the present invention, alpha amylase activity can be determined using an alpha amylase assay kit, e.g., available from Kikkoman Biochemifa Company, Cat No. 60213. See Materials and method section for detail. 1U=1 μmol CNP released/min. at 30° C., pH 4.0. Alternatively other suitable methods for determining alpha amylases activity may be used.

The variant polypeptides of the present invention have at least 20%, e.g., at least 40%, at least 50%, at least 60%, at least 70%, at least 80%, at least 90%, at least 95%, and at least 100% of the alpha amylase activity of the mature polypeptide of the parent alpha amylase comprised in SEQ ID NO: 2. In one embodiment the mature alpha amylase consists of SEQ ID NO: 3.

Variant: The term "variant" means a polypeptide having alpha amylase activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding one or several, e.g. 1-3, amino acids adjacent an amino acid occupying a position. Preferably the alteration is a substitution. The variant polypeptides of the present invention have at least 20%, e.g., at least 40%, at least 50%, at least 60%, at least 70%, at least 80%, at least 90%, at least 95%, and at least 100% of the alpha amylase activity of the mature polypeptide of the parent alpha amylase, e.g., SEQ ID NO: 3.

Mutant: The term "mutant" means a polynucleotide encoding a variant.

Wild-Type Enzyme: The term "wild-type" alpha amylase means an alpha amylase expressed by a naturally occurring microorganism, such as a bacterium, yeast, or filamentous fungus found in nature.

Parent or Parent alpha amylase: The term "parent" or "parent alpha amylase" means an alpha amylase to which an alteration is made to produce the enzyme variants of the present invention. The parent may be a naturally occurring (wild-type) polypeptide or a variant thereof.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, or 100% pure by weight of the total polypeptide material present in the preparation. The variants of the present invention are preferably in a substantially pure form. This can be accomplished, for example, by preparing the variant by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one embodiment, the mature polypeptide is amino acids 34 to 471 of SEQ ID NO: 2 based on the SignalP (Nielsen et al., 1997, *Protein Engineering* 10:1-6) program that predicts amino acids 1 to 21 of SEQ ID NO: 2 are a signal peptide, and amino acids 22 to 33 are a propeptide. The mature polypeptide is disclosed as SEQ ID NO: 3.

Mature polypeptide coding sequence: The term "mature polypeptide coding sequence" means a polynucleotide that encodes a mature polypeptide having alpha amylase activity. In one aspect, the mature polypeptide coding sequence is nucleotides 100 to 1416 (including the stop codon) of SEQ ID NO: 1 based on the SignalP (Nielsen et al., 1997, *Protein Engineering* 10:1-6) that predicts nucleotides 1 to 63 of SEQ ID NO: 1 encode a signal peptide and nucleotides 64 to 99 encodes a propeptide.

Sequence Identity: The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has alpha amylase activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, or at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, or at least 99.5% pure by weight. The polynucleotides of the present invention are preferably in a substantially pure form.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic.

The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, thermal activity, thermostability, pH activity, pH stability, substrate/cofactor specificity, improved surface properties, product specificity, increased stability, improved stability under storage conditions, and chemical stability.

Improved thermostability: The term "improved thermostability" means a variant displaying improved residual alpha amylase activity after a period of incubation at elevated temperature relative to the parent, either in a buffer or under conditions such as those which exist during product storage/transport or conditions similar to those that exist during industrial use of the variant. A variant may or may not display an altered thermal activity profile relative to the parent. For example, a variant may have an improved ability to refold following incubation at an elevated temperature relative to the parent. A variant according to the present invention displays an improved residual activity compared to the parent Rhizomucor pusilus alpha-amylase, disclosed as the mature polypeptide of SEQ ID NO: 2, after incubation for 1 hour at 65° C. at pH3.5. Residual activity was measured as described in the examples.

In one aspect, the thermostability of the variant having alpha amylase activity is at least 1.05-fold, e.g., at least 1.1-fold, at least 1.5-fold, at least 1.8-fold, at least 2-fold, at least 5-fold, at least 10-fold, at least 15-fold, at least 20-fold, or at least 25-fold more thermostable than the parent when residual activity is compared using, e.g., the amylase activity kit available from Kikkoman Biochemifa Company, Cat No. 60213). Other suitable amylase assays may also be used.

Improved pH stability: The term "improved pH stability" means a variant displaying retention of alpha amylase activity after a period of incubation at a specific pH, which reduce the enzymatic activity of the parent. Variants according to the present invention may have improved tolerance at a pH below 4.7, such as below 4.5, particularly below 4.0, more particularly below 3.8, such as pH 3.5.

Improved storage stability: The term "improved storage stability" means a variant displaying improved residual alpha amylase activity relative to a parent alpha amylase after incubation for a period of time at a specific pH and temperature. The tested conditions include pH 4.0, at 40° C. for 3 to 10 days.

Conventions for Designation of Variants

For purposes of the present invention, the mature polypeptide comprised in SEQ ID NO: 2 is used to determine the corresponding amino acid residue in another alpha amylase. In one particular embodiment the mature polypeptide consists of the polypeptide of SEQ ID NO: 3 and the specific positions substituted according to the invention refer to the positions of SEQ ID NO 3. The amino acid sequence of another alpha amylase is therefore aligned with the mature polypeptide comprised in SEQ ID NO: 2, and based on the alignment, the amino acid position number corresponding to any amino acid residue in the mature polypeptide comprised in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later.

Identification of the corresponding amino acid residue in another alpha amylase can be confirmed by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567).

In describing the alpha amylase variants of the present invention, the nomenclature described below is adapted for ease of reference. The accepted IUPAC single letter or three letter amino acid abbreviations are employed.

Substitutions.

For an amino acid substitution, the following nomenclature is used: Original amino acid, position, substituted amino acid. Accordingly, the substitution of threonine with alanine at position 226 is designated as "Thr226Ala" or "T226A". Multiple substitutions are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr,Glu" represents a substitution of arginine with tyrosine or glutamic acid at position 170. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Parent Alpha Amylase

The parent alpha amylase may be (a) a polypeptide with at least 60% sequence identity with the mature polypeptide of SEQ ID NO: 2; (b) a polypeptide encoded by a polynucleotide with at least 60% sequence identity with the mature polypeptide coding sequence of SEQ ID NO: 1; or (c) a fragment of the mature polypeptide of SEQ ID NO: 2, which has alpha amylase activity.

In one embodiment, the parent has a sequence identity to the mature polypeptide of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%, which has alpha amylase activity. In one aspect, the amino acid sequence of the parent differs by no more than ten amino acids, e.g., by five amino acids, by four amino acids, by three amino acids, by two amino acids, and/or by one amino acid from the mature polypeptide of SEQ ID NO: 2. The parent preferably comprises or consists of the amino acid sequence of SEQ ID NO: 2. In another aspect, the parent comprises or consists of the mature polypeptide of SEQ ID NO: 2. In another aspect, the parent comprises or consists of amino acids 34 to 471 of SEQ ID NO: 2. Amino acids 34 to 471 of SEQ ID NO: 2 is also described herein as SEQ ID NO: 3.

In another embodiment, the parent is an allelic variant of the mature polypeptide of SEQ ID NO: 2.

In another embodiment, the parent is encoded by a polynucleotide with a sequence identity to the mature polypeptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%, which encodes a polypeptide having alpha amylase activity. In one aspect, the mature polypeptide coding sequence is nucleotides 100 to 1413 of SEQ ID NO: 1. In an embodiment, the parent is encoded by a polynucleotide comprising or consisting of nucleotides 100 to 1413 SEQ ID NO: 1.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a fungal alpha amylase. For example, the parent may be a filamentous fungal alpha amylase such as a *Rhizomucor* alpha amylase.

In another aspect, the parent is a *Rhizomucor pusillus* alpha amylase, e.g., the alpha amylase of SEQ ID NO: 2 or the mature polypeptide thereof. In another embodiment the parent is the alpha amylase mature polypeptide coding sequence deposited in DSM 15334.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook, Fritsch, and Maniatis, 1989, *Molecular Cloning, A Laboratory Manual*, 2d edition, Cold Spring Harbor, N.Y.).

The parent may be a hybrid polypeptide in which a portion of one polypeptide is fused at the N-terminus and/or the C-terminus of a portion of another polypeptide(s).

The parent may also be a fused polypeptide or cleavable fusion polypeptide in which one polypeptide is fused at the N-terminus and/or the C-terminus of another polypeptide(s). A fused polypeptide may be produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fused polypeptide is under control of the same promoter(s) and terminator. Fusion polypeptides may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In a most particular embodiment the hybrid polypeptide of the invention is a variant alpha amylase of the invention connected to a carbohydrate-binding module (CBM) via a linker. Such hybrids, comprising a polypeptide having alpha-amylase activity and a carbohydrate binding module, primarily having affinity for starch, have the advantage over existing alpha-amylases that by selecting a catalytic domain with desired properties e.g. the pH profile, the temperature profile, the oxidation resistance, the calcium stability, the substrate affinity or the product profile can be combined with a carbohydrate binding module with stronger or weaker binding affinities, e.g., specific affinities for amylose, specific affinities for amylopectin or affinities for specific structure in the carbohydrate.

Linker Sequence

The linker sequence may be any suitable linker sequence, e.g., a linker sequence derived from an alpha-amylase or a glucoamylase (GA) (also referred to as an amyloglucosidase (AMG)). The linker may be a bond, or a short linking group comprising from about 2 to about 100 carbon atoms, in particular of from 2 to 40 carbon atoms. However, the linker is preferably a sequence of from about 2 to about 100 amino acid residues, more preferably of from 4 to 40 amino acid residues, such as from 6 to 15 amino acid residues.

Preferably a hybrid polypeptidecomprises a linker sequence derived from any species selected from the group consisting of *Acremonium, Aspergillus, Athelia, Coniochaeta, Leucopaxillus, Meripilus, Pachykytospora, Penicillium, Sublispora, Trametes, Trichophaea*, and *Valsaria*. The linker may also be derived from a bacterium, e.g., from a strain within *Bacillus* sp. More preferably, the linker is derived from a species selected from the group consisting of *Acremonium* sp., *Coniochaeta* sp., *Meripilus giganteus, Penicillium* sp., *Sublispora provurvata, Trametes corrugata, Trichophaea saccata, Valsaria rubricosa, Valsario spartii, Aspergillus kawachii, Aspergillus niger, Athelia rolfsii, Leucopaxillus gigantus, Pachykytospora papayracea, Trametes cingulata* and *Bacillus flavothermus*.

Even more preferably the linker is a linker from a glucoamylase selected from the group consisting of *Pachykytospora papayracea* (e.g. SEQ ID NO: 8), *Trametes cingulata* (e.g. SEQ ID NO: 9), *Leucopaxillus gigantus* (e.g. SEQ ID NO: 10), *Athelia rolfsii* (e.g. SEQ ID NO: 19), *Aspergillus kawachii* (e.g. SEQ ID NO: 20), *Aspergillus niger* (e.g. SEQ ID NO: 21) or a linker from an alpha-amylase selected from the group consisting of *Sublispora provurvata* (e.g. SEQ ID NO: 12), *Valsaria rubricosa* (e.g. SEQ ID NO: 13), *Acremonium* sp. (e.g. SEQ ID NO: 14), *Meripilus giganteus* (e.g. SEQ ID NO: 15), *Bacillus flavothermus* (e.g. SEQ ID NO: 16, SEQ ID NO: 17 or SEQ ID NO: 18), *Coniochaeta* sp. AM603 (e.g. SEQ ID NO: 22), *Coniochaeta* sp. (e.g. SEQ ID NO: 23), *Trametes corrugata* (e.g. SEQ ID NO: 24), *Valsario spartii* (e.g. SEQ ID NO: 25), *Penicillium* sp. (e.g. SEQ ID NO: 26), *Trichophaea saccata* (e.g. SEQ ID NO: 11).

Also preferred for the invention is any linker amino acid sequence having at least 60%, at least 65%, at least 70%, at least 75%, at least 80%, at least 85%, at least 90% or even at least 95% identity to any sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26.

In another preferred embodiment the hybrid polypeptide has a linker sequence which differs from an amino acid sequences selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

For more details on the DNA encoding these linkers see WO 06/069290.

Carbohydrate-Binding Modules

A carbohydrate-binding module (CBM), or as often referred to, a carbohydrate-binding domain (CBD), is a polypeptide amino acid sequence which binds preferentially to a poly- or oligosaccharide (carbohydrate), frequently—but not necessarily exclusively—to a water-insoluble (including crystalline) form thereof.

CBMs derived from starch degrading enzymes are often referred to as starch-binding modules (SBM) or starch binding domains (SBD). CBMs may occur in certain amylolytic enzymes, such as certain glucoamylases (GA), or in enzymes such as cyclodextrin glucanotransferases, or in alpha-amylases. Likewise, other sub-classes of CBMs would embrace, e.g., cellulose-binding modules (CBMs from cellulolytic enzymes), chitin-binding modules (CBMs which typically occur in chitinases), xylan-binding modules (CBMs which typically occur in xylanases), mannan-binding modules (CBMs which typically occur in mannanases). SBMs are often referred to as SBDs (Starch Binding Domains).

CBMs are found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and one, two or three CBMs and optionally further comprise one or more polypeptide amino acid sequence regions linking the CBM(s) with the catalytic module(s), a region of the latter type usually being denoted a "linker". Examples of hydrolytic enzymes comprising a CBM—some of which have already been mentioned above—are cellulases, xylanases, mannanases, arabinofuranosidases, acetylesterases and chitinases. CBMs have also been found in algae, e.g., in the red alga *Porphyra purpurea* in the form of a non-hydrolytic polysaccharide-binding protein.

In proteins/polypeptides in which CBMs occur (e.g., enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

The "Carbohydrate-Binding Module of Family 20" or a CBM-20 module is in the context of this invention defined as a sequence of approximately 100 amino acids having at least 45% identity to the Carbohydrate-Binding Module (CBM) of the polypeptide disclosed in FIG. 1 by Joergensen et al., 1997, *Biotechnol. Lett.* 19:1027-1031. The CBM comprises the last 102 amino acids of the polypeptide, i.e., the subsequence from amino acid 582 to amino acid 683. The numbering of Glycoside Hydrolase Families follows the concept of Coutinho, P. M. & Henrissat, B. (1999) CAZy-Carbohydrate-Active Enzymes server at URL: afmb.cnrs-mrs.fr/~cazy/CAZY/index.html or alternatively Coutinho & Henrissat, 1999, The modular structure of cellulases and other carbohydrate-active enzymes: an integrated database approach. In *"Genetics, Biochemistry and Ecology of Cellulose Degradation"*, K. Ohmiya, K. Hayashi, K. Sakka, Y. Kobayashi, S. Karita and T. Kimura eds., Uni Publishers Co., Tokyo, pp. 15-23 and Bourne and Henrissat, 2001, Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

CBMs deriving from fungal, bacterial or plant sources will generally be suitable for use in the hybrid of the invention. Preferred are CBMs of fungal origin. In this connection, techniques suitable for isolating the relevant genes are well known in the art.

Preferred, are hybrids comprising a CBM of Carbohydrate-Binding Module Family 20, 21 or 25. CBMs of Carbohydrate-Binding Module Family 20 suitable for the invention which may be derived from glucoamylases of *Aspergillus awamori* (SWISSPROT Q12537), *Aspergillus kawachii* (SWISSPROT P23176), *Aspergillus niger* (SWISSPROT P04064), *Aspergillus oryzae* (SWISSPROT P36914), from alpha-amylases of *Aspergillus kawachii* (EMBL#AB008370), *Aspergillus nidulans* (NCBI AAF17100.1), from beta-amylases of *Bacillus cereus* (SWISSPROT P36924), or from CGTases of *Bacillus circulans* (SWISSPROT P43379).

Preferably the hybrid comprises a CBM which is derived from any family or species selected from the group consisting of *Acremonium, Aspergillus, Athelia, Coniochaeta, Cryptosporiopsis, Dichotomocladium, Dinemasporium, Diplodia, Gliocladium, Leucopaxillus, Malbranchea, Meripilus, Nectria, Pachykytospora, Penicillium, Rhizomucor, Rhizomucor pusillus, Streptomyces, Subulispora, Thermomyces, Trametes, Trichophaea saccata* and *Valsaria*. The CBM may also be derived from a plant, e.g., from corn (e.g., *Zea mays*) or a bacterium, e.g., *Bacillus*. More preferably the hybrid comprises a CBM derived from any species selected from the group consisting of *Acremonium* sp., *Aspergillus kawachii, Aspergillus niger, Aspergillus oryzae, Athelia rolfsii, Bacillus flavothermus, Coniochaeta* sp., *Cryptosporiopsis* sp., *Dichotomocladium hesseltinei, Dinemasporium* sp., *Diplodia* sp., *Gliocladium* sp., *Leucopaxillus gigantus, Malbranchea* sp, *Meripilus giganteus, Nectria* sp., *Pachykytospora papayracea, Penicillium* sp., *Rhizomucor pusillus, Streptomyces thermocyaneoviolaceus, Streptomyces limosus, Subulispora provurvata, Thermomyces lanuginosus, Trametes cingulata, Trametes corrugata, Trichophaea saccata, Valsaria rubricosa, Valsario spartii* and *Zea mays*.

Most preferably the hybrid comprises a CBM from a glucoamylase selected from the group consisting of *Pachykytospora papayracea* (SEQ ID NO: 28), *Trametes cingulata* (SEQ ID NO: 29), *Leucopaxillus gigantus* (SEQ ID NO: 30), *Athelia rolfsii* (SEQ ID NO: 36), *Aspergillus kawachii* (SEQ ID NO: 37), *Aspergillus niger* (SEQ ID NO: 38) or from an alpha-amylase selected from the group consisting of *Trichopheraea saccata* (SEQ ID NO: 27), *Subulispora provurvata*(SEQ ID NO: 31), *Valsaria rubricosa* (SEQ ID NO: 32), *Acremonium* sp. (SEQ ID NO: 33), *Meripilus giganteus* (SEQ ID NO: 34), *Bacillus flavothermus* (SEQ ID NO: 35), *Coniochaeta* sp. (SEQ ID NO: 39), *Zea mays* (SEQ ID NO: 40), *Coniochaeta* sp. (SEQ ID NO: 41), *Trametes corrugata* (SEQ ID NO: 42), *Valsario spartii* (SEQ ID NO: 43) and *Penicillium* sp. (SEQ ID NO: 44).

In another preferred embodiment the hybrid enzyme has a CBM sequence which differs from an amino acid sequences selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 and SEQ ID NO: 44 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Also preferred are CBMs having at least 60%, at least 65%, at least 70%, at least 75%, at least 80%, at least 85%, at least 90% or even at least 95% identity to any sequence selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 and SEQ ID NO: 44.

In a particularly preferred embodiment the variant alpha amylase of the invention is fused to the linker (SEQ ID NO: 19) and CBM (SEQ ID NO: 36) from *Athelia rolfsii* AMG (glucoamylase). This construct is shown in SEQ ID NO: 5 except that the catalytic core included in SEQ ID NO: 5 does not have any of the substitutions according to the invention and thus is identical to the parent alpha amylase shown as SEQ ID NO: 2. The DNA encoding SEQ ID NO: 5 is disclosed herein as SEQ ID NO: 4. More particularly the variant alpha amylase of the invention is fused to a linker and CBM having at least 60%, at least 65%, at least 70%, at least 75%, at least 80%, at least 85%, at least 90% or even at least 95% identity to the linker and CBM comprised in SEQ ID NO: 5.

In another particularly preferred embodiment the variant alpha amylase of the invention is fused to the linker (SEQ ID NO: 21) and CBM (SEQ ID NO: 38) from *Aspergillus niger* AMG. This construct is shown in SEQ ID NO: 7 except that the catalytic core included in SEQ ID NO: 7 does not have any of the substitutions according to the invention and thus is identical to the parent alpha amylase shown as SEQ ID NO: 2. The DNA sequence encoding the polypeptide of SEQ ID NO: 7 is disclosed herein as SEQ ID NO: 6. More particularly the variant alpha amylase of the invention is fused to a linker and CBM having at least 60%, at least 65%, at least 70%, at least 75%, at least 80%, at least 85%, at least 90% or even at least 95% identity to the linker and CBM comprised in SEQ ID NO: 7.

For more details about the DNA encoding the CBMs see WO 06/069290.

Preparation of Variants

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction may be accomplished by combining aspects of synthetic gene construction, and/or site-directed mutagenesis, and/or random mutagenesis, and/or shuffling. Semi-synthetic construction may be typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Variants

The present invention provides alpha amylase variants comprising an alteration at one or more (several) positions corresponding to positions 20, 76, 123, 128, 136, 141, 142, 143, 165, 192, 219, 224, 265, 383, and 410 of the mature polypeptide of SEQ ID NO: 2, wherein the variant has alpha amylase activity. Particularly the alteration is a substitution. In addition the variant may be selected from the group consisting of:

a) a polypeptide having at least 60% sequence identity to the mature polypeptide of SEQ ID NO: 2;

b) a polypeptide encoded by a polynucleotide that hybridizes under low stringency conditions with (i) the mature polypeptide coding sequence of SEQ ID NO: 1, or (ii) the full-length complementary strand of (i);

c) a polypeptide encoded by a polynucleotide with at least 60% identity with the mature polypeptide coding sequence of SEQ ID NO: 1; or d) a fragment of the mature polypeptide of SEQ ID NO: 2, which has alpha amylase activity.

In an embodiment, the variant has at least 60%, e.g., at least 65%, at least 70%, at least 75%, at least 80%, at least 85%, at least 90%, at least 95%, such as at least 96%, at least 97%, at least 98%, and/or at least 99%, but less than 100%, sequence identity with the mature polypeptide of SEQ ID NO: 2. In one aspect, the number of substitutions in the variants of the present invention is 1-20, e.g., 1-10 and 1-5, such as 1, 2, 3, 4, 5, 6, 7, 8, 9 or 10 substitutions.

In another embodiment, the variant is encoded by a polynucleotide having a sequence identity of at least 60%, e.g., at least 65%, at least 70%, at least 75%, at least 80%, at least 85%, at least 90%, at least 95%, at least 96%, at least 97%, at least 98%, or at least 99%, but less than 100%, to the mature polypeptide coding sequence of SEQ ID NO: 1.

In another embodiment, the variant is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complementary strand of (i) (Sambrook, Fritsch, and Maniatis, 1989, *Molecular Cloning, A Laboratory Manual,* 2d edition, Cold Spring Harbor, N.Y.).

The polynucleotide of SEQ ID NO: 1 or a subsequence thereof, as well as the amino acid sequence of SEQ ID NO: 2 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is used in a Southern blot.

For purposes of the present invention, hybridization indicates that the polynucleotide hybridizes to a labeled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 100 to 1413 of SEQ ID NO: 1. In another aspect, the nucleic acid probe is a polynucleotide that encodes the mature polypeptide of SEQ ID NO: 2 or a fragment thereof. In another aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SSC plus 0.1% SDS for 15 minutes and twice each for 15 minutes using 6×SSC at 5° C. to 10° C. below the calculated $T_m$.

In another embodiment the variant is a fragment of the mature polypeptide of SEQ ID NO: 2 having a substitution at one or more positions corresponding to positions 128, 143, 141, 192, 20, 76, 123, 136, 142, 165, 219, 224, 265, 383 and 410, which has alpha amylase activity containing e.g. at least 435 amino acid residues, e.g., at least 433 or e.g. at least 431 amino acid residues.

In one aspect, a variant comprises a substitution at one or more (several) positions corresponding to positions selected from 20, 76, 123, 128, 136, 141, 142, 143, 165, 192, 219, 224, 265, 383, and 410. In another aspect, a variant comprises a substitution at two positions corresponding to any of positions selected from 20, 76, 123, 128, 136, 141, 142, 143, 165, 192, 219, 224, 265, 383, and 410. In another aspect, a variant comprises a substitution at three positions corresponding to any of positions selected from 20, 76, 123, 128, 136, 141, 142, 143, 165, 192, 219, 224, 265, 383, and 410. In another aspect, a variant comprises a substitution at four positions corresponding to any of positions 2 selected from 0, 76, 123, 128, 136, 141, 142, 143, 165, 192, 219, 224, 265, 383, and 410. In another aspect, a variant comprises a substitution at five positions corresponding to any of positions selected from 20, 76, 123, 128, 136, 141, 142, 143, 165, 192, 219, 224, 265, 383, and 410. In another aspect, a variant comprises a substitution at six positions corresponding to any of positions selected from 20, 76, 123, 128, 136, 141, 142, 143, 165, 192, 219, 224, 265, 383, and 410. In another aspect, a variant comprises a substitution at seven positions corresponding to any of positions selected from 20, 76, 123, 128, 136, 141, 142, 143, 165, 192, 219, 224, 265, 383, and 410. In another aspect, a variant comprises a substitution at eight positions corresponding to any of positions selected from 20, 76, 123, 128, 136, 141, 142, 143, 165, 192, 219, 224, 265, 383, and 410. In another aspect, a variant comprises a substitution at nine positions corresponding to any of positions selected from 20, 76, 123, 128, 136, 141, 142, 143, 165, 192, 219, 224, 265, 383, and 410. In another aspect, a variant comprises a substitution at ten positions corresponding to any of positions selected from 20, 76, 123, 128, 136, 141, 142, 143, 165, 192, 219, 224, 265, 383, and 410. In another aspect, a variant comprises a substitution at eleven positions corresponding to any of positions selected from 20, 76, 123, 128, 136, 141, 142, 143, 165, 192, 219, 224, 265, 383, and 410. In another aspect, a variant comprises a substitution at twelve positions corresponding to any of positions selected from 20, 76, 123, 128, 136, 141, 142, 143, 165, 192, 219, 224, 265, 383, and 410. In another aspect, a variant comprises a substitution at thirteen positions corresponding to any of positions selected from 20, 76, 123, 128, 136, 141, 142, 143, 165, 192, 219, 224, 265, 383, and 410. In another aspect, a variant comprises a substitution at fourteen positions corresponding to any of positions selected from 20, 76, 123, 128, 136, 141, 142, 143, 165, 192, 219, 224, 265, 383, and 410. In another aspect, a variant comprises a substitution at each position corresponding to positions selected from 20, 76, 123, 128, 136, 141, 142, 143, 165, 192, 219, 224, 265, 383, and 410.

In a particular embodiment the variant comprises substitutions at positions 128 and 143. In another particular embodiment the variant comprises substitutions at positions 128 and 141. In another particular embodiment the variant comprises substitutions at positions 141 and 143.

In a particular embodiment the variant comprises substitutions at positions 128, 141, and 143. In another particular embodiment the variant comprises substitutions at positions 128, 141, and 192. In another particular embodiment the variant comprises substitutions at positions 128, 143 and 192. In another particular embodiment the variant comprises substitutions at positions 141, 143 and 192.

In another particular embodiment the variant comprises substitutions at positions 128, 141, 143 and 192.

In one aspect, the variant comprises a substitution at a position corresponding to position 20.

In another aspect, the amino acid at a position corresponding to position 20 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser.

In one aspect, the variant comprises a substitution at a position corresponding to position 76. In another aspect, the amino acid at a position corresponding to position 76 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly.

In one aspect, the variant comprises a substitution at a position corresponding to position 123. In another aspect, the amino acid at a position corresponding to position 123 is substituted with Ala, Arg, Asn, Asp, Cys, Gln, Glu, Gly, His, Ile, Leu, Lys, Met, Phe, Pro, Ser, Thr, Trp, Tyr, or Val, preferably with His.

In one aspect, the variant comprises a substitution at a position corresponding to position 128. In another aspect, the amino acid at a position corresponding to position 128 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp.

In one aspect, the variant comprises a substitution at a position corresponding to position 136. In another aspect, the amino acid at a position corresponding to position 136 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe.

In another aspect, the variant comprises a substitution at a position corresponding to position 141. In another aspect, the amino acid at a position corresponding to position 141 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp.

In one aspect, the variant comprises a substitution at a position corresponding to position 141. In another aspect, the amino acid at a position corresponding to position 141 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg.

In another aspect, the variant comprises a substitution at a position corresponding to position 142. In another aspect, the amino acid at a position corresponding to position 142 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp.

In another aspect, the variant comprises a substitution at a position corresponding to position 143. In another aspect, the amino acid at a position corresponding to position 143 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn.

In one aspect, the variant comprises a substitution at a position corresponding to position 165. In another aspect, the amino acid at a position corresponding to position 165 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met.

In another aspect, the variant comprises a substitution at a position corresponding to position 192. In another aspect, the amino acid at a position corresponding to position 192 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg.

In another aspect, the variant comprises a substitution at a position corresponding to position 219. In another aspect, the amino acid at a position corresponding to position 219 is substituted with Ala, Arg, Asn, Asp, Cys, Gln, Glu, Gly, H is, Ile, Leu, Lys, Met, Phe, Pro, Ser, Thr, Trp, Tyr, or Val, preferably with Cys.

In one aspect, the variant comprises a substitution at a position corresponding to position 224. In another aspect, the amino acid at a position corresponding to position 224 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala.

In one aspect, the variant comprises a substitution at a position corresponding to position 224. In another aspect, the amino acid at a position corresponding to position 224 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg.

In one aspect, the variant comprises a substitution at a position corresponding to position 265. In another aspect, the amino acid at a position corresponding to position 265 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys.

In one aspect, the variant comprises a substitution at a position corresponding to position 383. In another aspect, the amino acid at a position corresponding to position 383 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg.

In another aspect, the variant comprises a substitution at a position corresponding to position 410. In another aspect, the amino acid at a position corresponding to position 410 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala.

In another aspect, the variant comprises the substitution G20S of the mature polypeptide of SEQ ID NO: 2. In another aspect, the variant comprises the substitution A76G of the mature polypeptide of SEQ ID NO: 2. In another aspect, the variant comprises the substitution S123H of the mature polypeptide of SEQ ID NO: 2. In another aspect, the variant comprises the substitution G128D of the mature polypeptide of SEQ ID NO: 2. In another aspect, the variant comprises the substitution K136F of the mature polypeptide of SEQ ID NO: 2. In another aspect, the variant comprises the substitution Y141W of the mature polypeptide of SEQ ID NO: 2. In another aspect, the variant comprises the substitution Y141R of the mature polypeptide of SEQ ID NO: 2. In another aspect, the variant comprises the substitution N142D of the mature polypeptide of SEQ ID NO: 2. In another aspect, the variant comprises the substitution D143N of the mature polypeptide of SEQ ID NO: 2. In another aspect, the variant comprises the substitution D165M of the mature polypeptide of SEQ ID NO: 2. In another aspect, the variant comprises the substitution K192R of the mature polypeptide of SEQ ID NO: 2. In another aspect, the variant comprises the substitution P219C of the mature polypeptide of SEQ ID NO: 2. In another aspect, the variant comprises the substitution P224A of the mature polypeptide of SEQ ID NO: 2. In another aspect, the variant comprises the substitution P224R of the mature polypeptide of SEQ ID NO: 2. In another aspect, the variant comprises the substitution A265C of the mature polypeptide of SEQ ID NO: 2. In another aspect, the variant comprises the substitution N383R of the mature polypeptide of SEQ ID NO: 2. In another aspect, the variant comprises the substitution V410A of the mature polypeptide of SEQ ID NO: 2.

In another aspect, the variant comprises the substitution Y141W of the mature polypeptide of SEQ ID NO: 2.

In another aspect, the variant comprises the substitution Y141R of the mature polypeptide of SEQ ID NO: 2.

In another aspect, the variant comprises the substitution K136F of the mature polypeptide of SEQ ID NO: 2.

In another aspect, the variant comprises the substitution K192R of the mature polypeptide of SEQ ID NO: 2.

In another aspect, the variant comprises the substitution P224A of the mature polypeptide of SEQ ID NO: 2.

In another aspect, the variant comprises the substitution P224R of the mature polypeptide of SEQ ID NO: 2.

In another aspect, the variant comprises the substitutions S123H+Y141W of the mature polypeptide of SEQ ID NO: 2.

In another aspect, the variant comprises the substitutions G20S+Y141W of the mature polypeptide of SEQ ID NO: 2.

In another aspect, the variant comprises the substitutions A76G+Y141W of the mature polypeptide of SEQ ID NO: 2.

In another aspect, the variant comprises the substitutions G128D+Y141W of the mature polypeptide of SEQ ID NO: 2.

In another aspect, the variant comprises the substitutions G128D+D143N of the mature polypeptide of SEQ ID NO: 2.

In another aspect, the variant comprises the substitutions Y141W+D143N of the mature polypeptide of SEQ ID NO: 2.

In another aspect, the variant comprises the substitutions Y141W+K192R of the mature polypeptide of SEQ ID NO: 2.

In another aspect, the variant comprises the substitutions Y141W+P219C of the mature polypeptide of SEQ ID NO: 2.

In another aspect, the variant comprises the substitutions Y141W+N383R of the mature polypeptide of SEQ ID NO: 2.

In another aspect, the variant comprises the substitutions N142D+D143N of the mature polypeptide of SEQ ID NO: 2.

In another aspect, the variant comprises the substitutions G128D+Y141W+D143N of the mature polypeptide of SEQ ID NO: 2.

In another aspect, the variant comprises the substitutions Y141W+N142D+D143N of the mature polypeptide of SEQ ID NO: 2.

In another aspect, the variant comprises the substitutions Y141W+D143N+K192R of the mature polypeptide of SEQ ID NO: 2.

In another aspect, the variant comprises the substitutions Y141W+D143N+P219C of the mature polypeptide of SEQ ID NO: 2.

In another aspect, the variant comprises the substitutions Y141W+K192R+V410A of the mature polypeptide of SEQ ID NO: 2.

In another aspect, the variant comprises the substitutions Y141W+P219C+A265C of the mature polypeptide of SEQ ID NO: 2.

In another aspect, the variant comprises the substitutions G128D+D143N+K192R of the mature polypeptide of SEQ ID NO: 2.

In another aspect, the variant comprises the substitutions G128D+Y141W+D143N+K192R of the mature polypeptide of SEQ ID NO: 2.

In another aspect, the variant comprises the substitutions G128D+D143N+K192R+P219C+Y141W of the mature polypeptide of SEQ ID NO: 2.

In another aspect, the variant comprises the substitutions Y141W+D143N+K192R+P219C of the mature polypeptide of SEQ ID NO: 2.

The variants may further comprise one or more additional alterations at one or more (e.g., several) other positions.

The amino acid changes may be of a minor nature, that is conservative amino acid substitutions, deletions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a parent can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha amylase activity to identify amino acid residues that are critical to the activity of the molecule. See also, Hilton et al., 1996, *J. Biol. Chem.* 271: 4699-4708. The active site of the alpha amylase or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent.

In one embodiment, the variant has improved pH stability compared to the parent enzyme.

In one embodiment, the variant has improved storage stability compared to the parent enzyme.

In one embodiment, the variant has improved thermostability compared to the parent enzyme.

Polynucleotides

The present invention also relates to isolated polynucleotides that encode any of the variants of the present invention.

Nucleic Acid Constructs

The present invention also relates to nucleic acid constructs comprising a polynucleotide encoding a variant of the present invention operably linked to one or more (several) control sequences that direct the expression of the coding sequence in a suitable host cell under conditions compatible with the control sequences.

A polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra.

Examples of suitable promoters for directing the transcription of the nucleic acid constructs of the present invention in a filamentous fungal host cell are the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* alpha-glucosidase, *Aspergillus niger* glucoamylase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide regions are present at the N-terminus of a variant, the propeptide region is positioned next to the N-terminus of the variant and the signal peptide region is positioned next to the N-terminus of the propeptide region.

It may also be desirable to add regulatory sequences that allow the regulation of the expression of the variant relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus licheniformis* or *Bacillus subtilis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and/or 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain substantially pure variants.

Host Cells

The present invention also relates to recombinant host cells, comprising a polynucleotide of the present invention operably linked to one or more (several) control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any gram-positive or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell, including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991,

*Microbios* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chtysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for the expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods may include use of specific antibodies, formation of an enzyme product, or disappearance of an enzyme substrate. For example, an enzyme assay may be used to determine the activity of the variant.

The variant may be recovered by methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure variants.

In an alternative aspect, the variant is not recovered, but rather a host cell of the present invention expressing a variant is used as a source of the variant.

Compositions

The present invention also relates to compositions comprising a variant of the present invention. Preferably, the compositions are enriched in such a variant. The term "enriched" means that the alpha amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. In a particular embodiment the composition comprises an amylase variant according to the invention and one or more enzymes selected from the group consisting of a protease, a glucoamylase.

The additional enzyme(s) may be produced, for example, by a microorganism belonging to the genus *Aspergillus*, e.g., *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, or *Aspergillus oryzae*; *Fusarium*, e.g., *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, e.g., *Humicola insolens* or *Humicola lanuginosa*; or *Trichoderma*, e.g., *Trichoderma harzianum*, *Trichoderma koningii*, *Trichoderma longibrachiatum*, *Trichoderma reesei*, or *Trichoderma viride*.

The compositions may be prepared in accordance with methods known in the art and may be in the form of a liquid or a dry composition. For instance, the composition may be in the form of a granulate or a microgranulate. The variant may be stabilized in accordance with methods known in the art.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more (several) expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiol*. 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

Uses

The present invention is also directed to processes/methods for using the polypeptides having alpha amylase activity of the invention.

Uses according to the invention include conversion of starch to, e.g., syrup and fermentation products, including ethanol and beverages. Examples of processes where an alpha amylase of the invention may be used include the ones described below and other processes for ethanol production known in the art which requires hydrolysis of starch-containing material.

Production of Fermentation Products

Process for Producing Fermentation Products from Gelatinized Starch-Containing Material In this aspect the present invention relates to a process for producing a fermentation product, especially ethanol, from starch-containing material, which process includes a liquefaction step and sequentially or simultaneously performed saccharification and fermentation steps.

The invention relates to a method for producing a fermentation product from starch-containing material comprising the steps of:

(a) liquefying starch-containing material using an alpha-amylase of the invention;

(b) saccharifying the liquefied material obtained in step (a) using a glucoamylase; and (c) fermenting the saccharified material using a fermenting organism.

The fermentation product, such as especially ethanol, may optionally be recovered after fermentation, e.g., by distillation. Suitable starch-containing starting materials are listed in the section "Starch-containing materials" section below. Contemplated enzymes are listed in the "Enzymes" section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms" section below. In preferred embodiments step (b) and (c) are carried out sequentially or simultaneously (i.e., as SSF process).

In a particular embodiment, the process of the invention further comprises, prior to the step (a), the steps of:

x) reducing the particle size of the starch-containing material, preferably by milling; and y) forming a slurry comprising the starch-containing material and water.

The aqueous slurry may contain from 10-40 wt. %, preferably 25-35 wt. % starch-containing material. The slurry is heated to above its gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C., for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) may include, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-Gelatinized Starch-Containing In this aspect the invention relates to processes for producing a fermentation product from starch-containing material without gelatinization of the starch-containing material (i.e., uncooked starch-containing material). According to the invention the desired fermentation product, such as ethanol, can be produced without liquefying the aqueous slurry containing the starch-containing material. In one embodiment a process of the invention includes saccharifying (milled) starch-containing material, e.g., granular starch, below its gelatinization temperature in the presence of an alpha amylase of the invention to produce sugars that can be fermented into the desired fermentation product by a suitable fermenting organism. In another embodiment a glucoamylase and an alpha amylase of the invention is used during saccharification and fermentation. Particularly the glucoamylase is *Trametes cingulata* AMG and the alpha amylase is the amylase of the invention preferentially including a linker and a CBD. In still another embodiment a protease, an alpha amylase and a debranching enzyme (e.g. a pullulanase or a glucoamylase) are used before the saccharification and fermentation.

Accordingly, in one aspect the invention relates to a method for producing a fermentation product from starch-containing material comprising:

(a) saccharifying starch-containing material with a glucoamylase and an alpha amylase according to the invention, at a temperature below the initial gelatinization temperature of said starch-containing material, (b) fermentingusing a fermenting organism.

Steps (a) and (b) of the process of the invention may be carried out sequentially or simultaneously. In an embodiment, a slurry comprising water and starch-containing material, is prepared before step (a).

The fermentation process may be carried out for a period of 1 to 250 hours, preferably from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species from which the starch-containing material is obtained, as well as with the growth conditions. In the context of this invention the initial gelatinization temperature of a given starch-containing material is the temperature at which birefringence is lost in 5% of the starch granules using the method described by Gorinstein and Lii, 1992, *Starch/Stärke* 44(12): 461-466.

Before step (a) a slurry of starch-containing material, such as granular starch, having 10-55 wt. % dry solids, preferably 25-40 wt. % dry solids, more preferably 30-35 wt. % dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol. % stillage, preferably 15-60% vol. % stillage, especially from about 30 to 50 vol. % stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low level such as below 6 wt. %, preferably below about 3 wt. %, preferably below about 2 wt. %, more preferred below about 1 wt. %., even more preferred below about 0.5 wt. %, or even more preferred 0.25 wt. %, such as below about 0.1 wt. %. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt. % or below about 0.2 wt. %. The process of the invention may be carried out at a pH in the range between 3 and 7, preferably from pH 3.5 to 6, or more preferably from pH 4 to 5.

Starch-Containing Materials

Any suitable starch-containing starting material, including granular starch, may be used according to the present invention. The starting material is generally selected based on the desired fermentation product. Examples of starch-containing starting materials, suitable for use in a process of present invention, include tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is reduced in particle size, preferably by dry or wet milling, in order to expose more surface area. In an embodiment the particle size is between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. Commercially available yeast include, e.g., Red Star™/ Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Enzymes

Glucoamylases

The term "glucoamylase" (1,4-alpha-D-glucan glucohydrolase, EC 3.2.1.3) is an enzyme, which catalyzes the release of D-glucose from the non-reducing ends of starch or related oligo- and polysaccharide molecules.

A glucoamylase may be derived from any suitable source, e.g., derived from a microorganism or a plant. Preferred glucoamylases are of fungal or bacterial origin. Examples of suitable glucoamylases include *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus glucoamylase* variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in positions A435 and S436 (Li et al., 1997, *Prot. Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces duponti, Talaromyces emersonii* (WO 99/28448), *Talaromyces leycettanus* (U.S. Pat. No. Re. 32,153), and *Talaromyces thermophilus* (U.S. Pat. No. 4,587,215), *Trametes cingulata, Pachykytospora papyracea*, and *Leucopaxillus giganteus*, all disclosed in WO 2006/069289; or *Peniophora rufomarginata* disclosed in PCT/US2007/066618; or a mixture thereof.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™, and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Alpha-Amylases

The variant alpha-amylase according to the invention has been described in detail above. Other alpha-amylases of fungal or bacterial origin may also be relevant in combination with the alpha amylase of the invention.

In a preferred embodiment an additional alpha-amylase is an acid alpha-amylase, e.g., fungal acid alpha-amylase or bacterial acid alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

A bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NO: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acid in position 179 to 182, preferably a double deletion disclosed in WO 96/23873—see, e.g., page 20, lines 1-10 (hereby incorporated by reference), preferably corresponding to delta(181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type *Bacillus stearothermophilus* alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, EC 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 3 in WO 99/19467) and the 37 N-terminal amino acid residues of the alpha-amylase derived from *Bacillus amyloliquefaciens* (shown as SEQ ID NO: 5 in WO 99/19467), with one or more, especially all, of the following substitutions: G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art.

Fungal Alpha-Amylases

Fungal acid alpha-amylases include acid alpha-amylases derived from a strain of the genus *Aspergillus*, such as *Aspergillus oryzae, Aspergillus niger*, or *Aspergillus kawachii* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TrEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated.

In a preferred embodiment the alpha-amylase is derived from *Aspergillus kawachii* and disclosed by Kaneko et al., 1996, *J. Ferment. Bioeng.* 81:292-298, "Molecular-cloning and determination of the nucleotide-sequence of a gene encoding an acid-stable alpha-amylase from *Aspergillus kawachii*"; and further as EMBL#AB008370.

The fungal acid alpha-amylase may also be a wild-type enzyme comprising a carbohydrate-binding module (CBM) and an alpha-amylase catalytic domain (i.e., a non-hybrid), or a variant thereof. In an embodiment the wild-type acid alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Application Publication no. 2005/0054071 (Novozymes) or U.S. patent application no. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in U.S. application No. 60/638,614 including Fungamyl variant with catalytic domain JA118 and *Athelia rolfsii* SBD (SEQ ID NO: 100 in U.S. application No. 60/638,614), *Rhizomucor pusillus* alpha-amylase with *Athelia rolfsii* AMG linker and SBD (SEQ ID NO: 101 in U.S. application No. 60/638,614) and *Meripilus giganteus* alpha-amylase with *Athelia rolfsii* glucoamylase linker and SBD (SEQ ID NO: 102 in U.S. application No. 60/638,614).

Other specific examples of contemplated hybrid alpha-amylases include those disclosed in U.S. Application Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, SPEZYME™ Ethyl, GC358, GC980, SPEZYME™ RSL, and SPEZYME™ DELTA AA (Genencor Int.).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

LIST OF PREFERRED EMBODIMENTS

1. An alpha amylase variant, comprising a substitution, at one or more positions corresponding to positions 128, 143, 141, 192, 20, 76, 123, 136, 142, 165, 219, 224, 265, 383, and 410 of the mature polypeptide of SEQ ID NO: 2, wherein the variant has alpha amylase activity.

2. The variant of claim 1, selected from the group consisting of:
    a) a polypeptide having at least 60% sequence identity to the mature polypeptide of SEQ ID NO: 2;
    b) a polypeptide encoded by a polynucleotide that hybridizes under low stringency conditions with (i) the mature polypeptide coding sequence of SEQ ID NO: 1, or (ii) the full-length complementary strand of (i);
    c) a polypeptide encoded by a polynucleotide with at least 60% identity with the mature polypeptide coding sequence of SEQ ID NO: 1; or
    d) a fragment of the mature polypeptide of SEQ ID NO: 2, which has alpha amylase activity.

3. The variant of embodiment 2, wherein the variant alpha amylase has at least 60%, e.g., at least 65%, at least 70%, at least 75%, at least 80%, at least 85%, at least 90%, at least 95%, at least 96%, at least 97%, at least 98%, or at least 99% sequence identity with the mature polypeptide of SEQ ID NO: 2.

4. The variant of any of embodiments 2-3, wherein the variant alpha amylase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1 or (ii) the full-length complementary strand of (i).

5. The variant of any of embodiments 2-4, wherein the variant alpha amylase is encoded by a polynucleotide with at least 60%, e.g., at least 65%, at least 70%, at least 75%, at least 80%, at least 85%, at least 90%, at least 95%, at least 96%, at least 97%, at least 98%, or at least 99% sequence identity with the mature polypeptide coding sequence of SEQ ID NO: 1.

6. The variant of any of embodiments 2-5, wherein the variant alpha amylase consists of the mature polypeptide of SEQ ID NO: 2 having a substitution, at one or more positions corresponding to positions 128, 143, 141, 192, 20, 76, 123, 136, 142, 165, 219, 224, 265, 383, and 410 of the mature polypeptide of SEQ ID NO: 2, and wherein the variant has alpha amylase activity.

7. The variant of any of embodiments 2-6, wherein the variant alpha amylase is a fragment of the mature polypeptide of SEQ ID NO: 2, wherein the fragment has alpha amylase activity.

8. The variant of any of embodiments 1-7, which is a variant of a parent alpha amylase selected from the group consisting of:
    a) a polypeptide having at least 60% sequence identity to the mature polypeptide of SEQ ID NO: 2;
    b) a polypeptide encoded by a polynucleotide with at least 60% identity with the mature polypeptide coding sequence of SEQ ID NO: 1; or
    c) a fragment of the mature polypeptide of SEQ ID NO: 2, which has alpha amylase activity.

9. The variant of any of embodiments 2-8, wherein the parent alpha amylase has at least 60%, e.g., at least 65%, at least 70%, at least 75%, at least 80%, at least 85%, at least 90%, at least 95% identity, at least 96%, at least 97%, at least 98%, at least 99%, but less than 100%, sequence identity to the mature polypeptide coding sequence of SEQ ID NO: 1.

10. The variant of any of embodiments 2-9, wherein the parent has at least 60%, e.g., at least 65%, at least 70%, at least 75%, at least 80%, at least 85%, at least 90%, at least 95%, at least 96%, at least 97%, at least 98%, and/or at least 99%, but less than 100% sequence identity with the mature polypeptide of SEQ ID NO: 2.

11. The variant of any of the preceding embodiments, wherein the mature polypeptide of SEQ ID NO: 2 is the polypeptide of SEQ ID NO: 3.

12. The variant of any of embodiments 1-11, wherein the number of alterations is 1-20, e.g., 1-10 and/or 1-5, such as 1, 2, 3, 4, 5, 6, 7, 8, 9 or 10 alterations.

13. The variant according to any of embodiments 1-12, wherein the variant further comprises a linker and a carbohydrate binding module.

14. The variant of any of embodiments 1-13, which comprises a substitution at a position corresponding to position 20.

15. The variant of embodiment 14, wherein the alteration is a substitution with Ser.
16. The variant of any of embodiments 1-15, which comprises a substitution at a position corresponding to position 76.
17. The variant of embodiment 16, wherein the alteration is a substitution with Gly.
18. The variant of any of embodiments 1-17, which comprises a substitution at a position corresponding to position 123.
19. The variant of embodiment 18, wherein the alteration is a substitution with His.
20. The variant of any of embodiments 1-19, which comprises a substitution at a position corresponding to position 128.
21. The variant of embodiment 20, wherein the alteration is a substitution with Asp.
22. The variant of any of embodiments 1-21, which comprises a substitution at a position corresponding to position 136.
23. The variant of embodiment 22, wherein the alteration is a substitution with Phe.
24. The variant of any of embodiments 1-23, which comprises a substitution at a position corresponding to position 141.
25. The variant of embodiment 24, wherein the alteration is a substitution with Trp or Arg.
26. The variant of any of embodiments 1-25, which comprises a substitution at a position corresponding to position 142.
27. The variant of embodiment 26, wherein the alteration is a substitution with Asp.
28. The variant of any of embodiments 1-27, which comprises a substitution at a position corresponding to position 143.
29. The variant of embodiment 28, wherein the alteration is a substitution with Asn.
30. The variant of any of embodiments 1-29, which comprises a substitution at a position corresponding to position 165.
31. The variant of embodiment 30, wherein the alteration is a substitution with Met.
32. The variant of any of embodiments 1-31, which comprises a substitution at a position corresponding to position 192.
33. The variant of embodiment 32, wherein the alteration is a substitution with Arg.
34. The variant of any of embodiments 1-33, which comprises a substitution at a position corresponding to position 219.
35. The variant of embodiment 34, wherein the alteration is a substitution with Cys.
36. The variant of any of embodiments 1-35, which comprises a substitution at a position corresponding to position 224.
37. The variant of embodiment 36, wherein the alteration is a substitution with Ala or Arg.
38. The variant of any of embodiments 1-37, which comprises a substitution at a position corresponding to position 265.
39. The variant of embodiment 38, wherein the alteration is a substitution with Cys.
40. The variant of any of embodiments 1-39, which comprises a substitution at a position corresponding to position 383.
41. The variant of embodiment 40, wherein the alteration is a substitution with Arg.
42. The variant of any of embodiments 1-41, which comprises a substitution at a position corresponding to position 410.
43. The variant of embodiment 42, wherein the alteration is a substitution with Ala.
44. The variant of any of embodiments 1-43, which comprises a substitution at two positions corresponding to any of positions 20, 76, 123, 128, 136, 141, 142, 143, 165, 192, 219, 224, 265, 383, and 410.
45. The variant of any of embodiments 1-44, which comprises a substitution at three positions corresponding to any of positions 20, 76, 123, 128, 136, 141, 142, 143, 165, 192, 219, 224, 265, 383, and 410.
46. The variant of any of embodiments 1-45, which comprises a substitution at four positions corresponding to any of positions 20, 76, 123, 128, 136, 141, 142, 143, 165, 192, 219, 224, 265, 383, and 410.
47. The variant of any of embodiments 1-46, which comprises a substitution at five positions corresponding to any of positions 20, 76, 123, 128, 136, 141, 142, 143, 165, 192, 219, 224, 265, 383, and 410.
48. The variant of any of embodiments 1-47, which comprises a substitution at six positions corresponding to any of positions 20, 76, 123, 128, 136, 141, 142, 143, 165, 192, 219, 224, 265, 383, and 410.
49. The variant of any of embodiments 1-48, which comprises a substitution at each position corresponding to positions 20, 76, 123, 128, 136, 141, 142, 143, 165, 192, 219, 224, 265, 383, and 410.
50. The variant of any of embodiments 1-49, which comprises one or more (several) substitutions selected from the group consisting of G20S, A76G, S123H, G128D, K136F, Y141W, Y141R, N142D, D143N, D165M, K192R, P219C, P224A, P224R, A265C, N383R, and V410A.
51. The variant of embodiment 50, wherein the variant comprises at least one of the following substitutions or combinations of substitutions:
D165M; or
Y141W; or
Y141R; or
K136F; or
K192R; or
P224A; or
P224R; or
S123H+Y141W; or
G20S+Y141W; or
A76G+Y141W; or
G128D+Y141W; or
G128D+D143N; or
141W+P219C; or
N142D+D143N; or
Y141W+K192R; or
Y141W+D143N; or
Y141W+N383R; or
Y141W+P219C+A265C; or
Y141W+N142D+D143N; or
Y141W+K192R+V410A; or
G128D+Y141W+D143N; or
Y141W+D143N+P219C; or
Y141W+D143N+K192R; or
G128D+D143N+K192R; or
Y141W+D143N+K192R+P219C; or
G128D+Y141W+D143N+K192R; or
G128D+Y141W+D143N+K192R+P219C.
52. The variant according to any of embodiments 13-51, wherein the carbohydrate-binding module is a polypeptide comprising an amino acid sequence which has at least 60% identity with a sequence selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 and SEQ ID NO: 44.
53. The variant according to embodiment 52, wherein the linker and CBM is from *Athelia rolfsii* e.g., SEQ ID NO: 19 and SEQ ID NO: 36 or a sequence having 60% identity thereto.

54. The variant according to embodiment 52, wherein the linker and CBM is from *Aspergillus niger* e.g., SEQ ID NO: 21 and SEQ ID NO: 38 or a sequence having 60% identity thereto.

55. An isolated polynucleotide encoding the variant of any of embodiments 1-54.

56. A nucleic acid construct comprising the polynucleotide of embodiment 55.

57. An expression vector comprising the polynucleotide of embodiment 56.

58. A host cell comprising the polynucleotide of embodiment 57.

59. A method of producing a variant alpha amylase, comprising:
 a) cultivating the host cell of embodiment 57 under conditions suitable for the expression of the variant; and
 b) recovering the variant.

60. A transgenic plant, plant part or plant cell comprising the polynucleotide of embodiment 55.

61. A method of producing a variant of any of embodiments 1-54, comprising:
 a) cultivating a transgenic plant or a plant cell comprising a polynucleotide encoding the variant under conditions conducive for production of the variant; and
 b) recovering the variant.

62. A method for producing a fermentation product from starch-containing material comprising the steps of:
 (a) liquefying starch-containing material using a variant alpha-amylase according to any of the embodiments 1-54;
 (b) saccharifying the liquefied material obtained in step (a) using a glucoamylase; and
 (c) fermenting the saccharified material using a fermenting organism.

63. A method for producing a fermentation product from starch-containing material comprising:
 (a) saccharifying starch-containing material with a variant alpha amylase according to any of the embodiments 1-54, and a glucoamylase at a temperature below the initial gelatinization temperature of said starch-containing material,
 (b) fermenting using a fermenting organism.

64. The method according to any of embodiments 62 and 63, wherein the fermenting organism is a yeast organism, particularly a *Saccharomyces* spp, more particularly *Saccharomyces cerevisiae*.

65. The method according to any of embodiments 62-64, wherein the fermentation product is an alcohol, particularly ethanol.

66. A method for producing an enzymatically modified starch derivative, wherein a polypeptide having alpha-amylase activity according to any of embodiments 1-54 is used for liquefying and/or saccharifying starch.

Various references are cited herein, the disclosures of which are incorporated by reference in their entireties. The present invention is further described by the following examples which should not be construed as limiting the scope of the invention.

EXAMPLES

Example 1

Preparation of Variants, and Test for Thermostability

Strains and Plasmids

*E. coli* DH12S (available from Gibco BRL) was used for yeast plasmid rescue.

pLAV019 is a *S. cerevisiae* and *E. coli* shuttle vector under the control of TPI promoter, described in WO06069290, having the acid *Aspergillus niger* alpha-amylase signal sequence, the *Rhizomucor pusilus* alpha-amylase gene and the partial *Athelia rolfsii* glucoamylase gene sequence comprising only the linker and the CBM. The vector was used to construct protein engineering libraries and site-directed variants.

*Saccharomyces cerevisiae* YNG318: MATa Dpep4[cir+] ura3-52, leu2-D2, h is 4-539 was used for alpha-amylase variants expression. It is described in *J. Biol. Chem.* 272(15): 9720-9727 (1997).

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar and $H_2O$ (approx. 761 ml) is autoclaved together, and the separately sterilized SC-glucose solution added to the agar solution.

SC-glucose+starch plate: 0.5-0.8% of corn starch is added to the above SC-glucose medium containing 2% agar.

YPD: Bacto peptone 20 g/l, yeast extract 10 g/l, 20% glucose 100 ml/l.

PEG/LiAc solution: 40% PEG4000 50 ml, 5 M Lithium Acetate 1 ml

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.

Yeast Transformation

Yeast transformation was carried out by lithium acetate method. Mix 0.5 microL of vector (digested by restriction endonucleases) and 1 microL of PCR fragments. Thaw YNG318 competent cells on ice. Mix 100 microL of the cells, the DNA mixture and 10 microL of YEAST MAKER carrier DNA (Clontech) in 12 ml polypropylene tubes (Falcon 2059). Add 0.6 ml PEG/LiAc solution and mix gently. Incubate for 30 min at 30° C., and 200 rpm. Incubate for 30 min at 42° C. (heat shock). Transfer to a microfuge tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to make colonies. Yeast total DNA was extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor, Sambrook et al., 1989, supra) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Yeast Library and Site-Directed Variants

Library in yeast and site-directed variants were constructed by SOE PCR method (Splicing Overlap Extension, see "PCR: A practical approach", p. 207-209, Oxford University press, 1991, eds. McPherson, Quirke, Taylor), followed by yeast in vivo recombination.

The below primers are used to make DNA fragments containing any mutated fragments by the SOE method together with degenerate primers (AM34+Reverse primer and AM35+ forward primer) or just to amplify a whole amylase gene (AM34+AM35). AM34 and AM35 are primers located at the up-stream and down-stream of the amylase gene.

```
AM34    TAGGAGTTTAGTGAACTTGC    (SEQ ID NO: 45)
AM35    TTCGAGCGTCCCAAAACC      (SEQ ID NO: 46)
```

| PCR reaction system: | | Conditions: |
|---|---|---|
| 48.5 micro L H2O | 1 | 94° C. 2 min |
| 2 beads puRe Taq Ready-To-Go PCR | 2 | 94° C. 30 sec |
| Beads (Amersham Biosciences) | 3 | 55° C. 30 sec |
| 0.5 micro L × 2 100 pmole/micro L | 4 | 72° C. 90 sec |
| Primers | 2-4 | 25 cycles |
| 0.5 micro L Template DNA | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Construction of Amylase Hybrids with Other Linker and CBM

Amylase hybrids comprising the *Rhizomucor pusilus* catalytic core fused to linkers and CBMs other than those from *Athelia rolfsii* glucoamylase were constructed by the SOE method utilizing yeast in vivo recombination.

The partial sequence encoding the CBM region of *Athelia rolfsii* was removed from the variant plasmids having the *Athelia rolfsii* glucoamylase linker and CBM by digesting with the restriction enzymes, SacI and NotI, and the resultant vector was mixed with the PCR fragment amplified using a pair of below primers from the *Aspergillus niger* glucoamylase gene. They were introduced into yeast to construct hybrids with the linker and CBM from the *Aspergillus niger* glucoamylase.

```
AN linker F   CGGCTATCTTCACCTCTGCTACTGGCGGCACCACTACG          (SEQ ID NO: 47)
AN linker R   CTAATTACATGATGCGGCCCGCGGCCGCCTACCGCCAGGTGTCAGTC (SEQ ID NO: 48)
```

Expression of Amylases with CBM in *Aspergillus niger*

The constructs comprising the alpha amylase variant genes including a linker and a CBM were used to construct expression vectors. The parental plasmid, pAspV019, consists of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The *Aspergillus* expression plasmids were transformed into *Aspergillus* as described in Lassen et al., 2001, *Applied and Environmental Microbiology* 67: 4701-4707. Transformants expressing V019 variants were isolated, purified and cultivated in shake flasks. The culture broths from fermentations of *Aspergillus niger* expressing amylase with CBM were purified by affinity purification (*Biochem. J.* 372: 905-910 (2003)).

Screening of Protein Engineered Libraries and Site-Directed Mutagenesis Variants Yeast clones on SC-glucose were re-inoculated onto SC-glucose plates containing starch and the clones showing clearing zones were inoculated into a well of a 24-well micro titre plate containing YPD medium, and cultivated at 28° C. for 3 days. 2 M sodium acetate buffer, pH3.5, was added to the culture supernatants to the final concentration at 100 mM, and incubated at 4 and 65° C. for 1 hour. The residual alpha-amylase activities were measured by Alpha-amylase assay kit (Kikkoman Biochemifa Company, Cat No. 60213), according to the supplier's protocol. The assay is based on degradation of N3-G5-β-CNP (2 chloro-4 nitrophenyl $6^5$-azide-$6^5$-deoxy-b-maltopentoside) by the alpha-amylase to release G3-β-CNP and G2-β-CNP, which are further degraded by glucoamylase and beta-glucosidase provided in the solutions in the kit to CNP. 1U of alpha-amylase activity was defined as 1 μmol CNP released/min at pH 4.0 and 30° C.

Unit/ml of each sample was calculated after incubation of part of the sample 1 hour at 4° C. and another part of the sample after incubation 1 hour at 65° C. In the table below the ratio between these two activities for each sample is shown as % residual activity. U/ml was calculated as: alpha-amylase activity=$(E_{sample}-E_{blank}) \times 0.179 \times$ dilution factor, wherein CPN released was detected by spectrophotometry at A400.

The clones with higher ratio of the activity after incubating at 65° C./activity after incubating at 4° C. than the parental variant were selected and the sequence was determined.

TABLE 1

Residual alpha-amylase activity of variants

| Variant No. | CBM | Substitutions | The ratio of the residual activity after incubating at 65° C./4° C. (the ratio of the parental amylase (either wild-type (WT) or another variant) |
|---|---|---|---|
| PE12 | AR (Ath. rolfsii) | D165M | 55% (WT 34%) |
| PE15 | AR | Y141R | 68% (WT 34%) |
| PE16 | AR | Y141W | 89% (WT 34%) |

TABLE 1-continued

Residual alpha-amylase activity of variants

| Variant No. | CBM | Substitutions | The ratio of the residual activity after incubating at 65° C./4° C. (the ratio of the parental amylase (either wild-type (WT) or another variant) |
|---|---|---|---|
| PE27 | AR | S123H + Y141W | 50% (WT 22%, PE16 40%) |
| PE30 | AR | G20S + Y141W | 43% (WT 18%, PE16 32%) |
| PE34 | AR | A76G + Y141W | 27% (WT 15%, PE16 30%) |
| PE36 | AR | G128D + Y141W | 31% (WT 15%, PE16 30%) |
| PE39 | AR | Y141W + P219C | 26% (PE16 18%) |
| PE41 | AR | N142D + D143N | 40% (PE16 18%) |
| PE53 | AR | Y141W + K192R | 57% (PE16 23%) |
| PE55 | AR | Y141W + P219C + A265C | 35% (PE16 28%) |
| PE57 | AR | Y141W + N142D + D143N | 55% (PE16 26%, PE41 46%) |
| PE58 | AR | Y141W + D143N | 66% (PE16 26%) |
| PE64 | AR | Y141W + N383R | 21% (PE16 15%) |
| PE65 | AR | Y141W + K192R + V410A | 55% (PE16 15%) |
| PE67 | AR | G128D + Y141W + D143N | 37% (PE16 8%, PE58 38%) |

TABLE 1-continued

Residual alpha-amylase activity of variants

| Variant No. | CBM | Substitutions | The ratio of the residual activity after incubating at 65° C./4° C. (the ratio of the parental amylase (either wild-type (WT) or another variant) |
|---|---|---|---|
| PE71 | AR | Y141W + D143N + K192R | 50% (PE16 8%, PE58 38%) |
| PE75 | AR | Y141W + D143N + K192R + P219C | 34% (PE16 23%) |
| PE77 | AR | G128D + Y141W + D143N + K192R | 57% (PE16 8%, PE58 38%) |
| PE79 | AR | G128D + Y141W + D143N + K192R + P219C | 37% (PE16 23%) |
| PE81 | AR | Y141W + D143N + K192R (=PE71) | 72% (PE16 31%, PE58 64%) |
| PE84 | AN (Asp. niger) | Y141W + D143N | 70% (WT 20%) |
| PE85 | AN | G128D + Y141W + D143N | 66% (WT 15%) |
| PE86 | AN | G128D + Y141W + D143N + K192R | 85% (WT 15%) |
| PE96 | AN | G128D + D143N | 65% (WT 20%) |
| PE97 | AN | K136F | 46% (WT 20%) |
| PE99 | AN | P224A | 26% (WT 20%) |
| PE100 | AN | P224R | 28% (WT 20%) |
| PE101 | AN | G128D + D143N + K192R | 79% (WT 16%) |
| PE122 | AN | K192R | 73% (WT 29%) |

As seen from the table all variants tested showed improved thermostability compared to the wild-type alpha amylase.

Example 2

Storage Stability of Variants

One of the variants, PE16, was expressed in *Aspergillus niger* and the culture supernatants were purified by a three-step chromatographic procedure: anion-exchange at pH 7.0 and pH 5.0 followed by size-exclusion chromatography. Two fractions with amylase activity, having Mw at ca. 50 kDa and 60 kDa which are corresponding to the molecules with cleaved of CBM (core part) and intact linker and CBM, were collected and tested for storage stability. The samples were incubated at pH 3.8, at 4° C. and 40° C. for 6 days and the remaining activities were measured each day.

TABLE 2

The results are given as relative residual activity

| Storage at pH 3.8 | Days | | | | |
|---|---|---|---|---|---|
| at 4° C. or 40° C. | 0 | 1 | 2 | 3 | 6 |
| wild type, 4° C. | 100% | 99% | 102% | 96% | 102% |
| wild type, 40° C. | 100% | 60% | 38% | 22% | 6% |
| PE16 (core part), 4° C. | 100% | 98% | 101% | 100% | 107% |
| PE16(core part), 40° C. | 100% | 79% | 62% | 48% | 25% |
| PE16, 4° C. | 100% | 97% | 99% | 98% | 104% |
| PE16, 40° C. | 100% | 76% | 59% | 45% | 21% |

The data demonstrate that presence of a linker and CBM does not affect the improvements obtained by introducing the substitutions according to the invention in the core region.

Example 3

Thermo Stability at pH 3.5

The thermo-stability of selected variants fusions including a linker and a CBD were evaluated using the following conditions.

1/20 (v/v) of 2 M Sodium acetate buffer, pH 3.5, was added to the yeast culture supernatants of clones expressing the selected alpha amylase variants and samples were incubated at 4, 60, 65 and 70° C. for 1 hour.

Residual activities were measured by the alpha-amylase assay kit (Kikkoman #60123) as described above and the resulting residual activities are relative to the activity at 4° C.

TABLE 3

Residual alpha amylase activity relative to the 4° C. samples.

| Enzyme | Linker & CBD | 60° C. | 65° C. | 70° C. |
|---|---|---|---|---|
| PE84 | A. niger AMG | 78% | 53% | 33% |
| PE85 | A. niger AMG | 80% | 48% | 33% |
| PE86 | A. niger AMG | 76% | 55% | 46% |
| PE96 | A. niger AMG | 73% | 48% | 25% |
| PE97 | A. niger AMG | 65% | 32% | 8% |
| PE100 | A. niger AMG | 58% | 19% | 2% |
| PE101 | A. niger AMG | 81% | 60% | 42% |
| WT | A. niger AMG | 53% | 13% | 1% |

Under the tested conditions all variants showed improved thermo-stability.

Example 4

Storage Stability of Variants at pH 4.0

Purified alpha amylase variants expressed in *Aspergillus oryzae* were incubated at 40° C. for 3 days and 10 days (4° C. as a control) under the following conditions:
50 mM NaOAc buffer (pH4.0)
0.5 mM CaCl2
0.005% Triton X-100

Residual activities were measured by the alpha-amylase assay kit (Kikkoman #60123) as described above.

TABLE 4

Residual alpha amylase activity

| Enzyme | Linkers & CBD | 3 days | 10 days |
|---|---|---|---|
| Wt | A. rolfsii AMG | 36% | 3% |
| Wt | A. niger AMG | 34% | 2% |
| PE67 | A. rolfsii AMG | 108% | 56% |
| PE85 | A. niger AMG | 110% | 54% |
| PE96 | A. niger AMG | 81% | 53% |
| PE77 | A. rolfsii AMG | 95% | 83% |
| PE86 | A. niger AMG | 97% | 78% |
| PE101 | A. niger AMG | 88% | 79% |

Under the tested conditions all variants showed improved storage stability.

Example 5

Test of Selected Variants in a Raw Starch Hydrolysis Based Ethanol Process

Approximately 405 g yellow dent corn (obtained from several Midwest-based corn to ethanol producers; ground in-house with Turkish grind setting) was added to 595 g tap water. This mixture was supplemented with 3 ppm penicillin and 1000 ppm urea. The slurry was adjusted to pH 4.5 with 40% $H_2SO_4$. Approximately 5 g of this slurry was added to 15 mL tubes. Each tube was dosed with 0.0801 mg/gDS glucoamylase from *Tramets cingulata* and 0.0225 mg/gDS alpha-amylase, followed by 200 µL of yeast propagate (0.024 g Fermentis Ethanol Red yeast, incubated overnight at 32° C. in 50 mL filtered liquefied corn mash and 5.1 µL Sprizyme Plus AMG). Water was added to each tube to bring the total added volume (enzyme+water) to 1.2% of the initial weight of the mash.

Tubes were incubated at 32° C. and six replicate fermentations of each treatment were run. All tubes were vortexed at 24, 48 and 70 hours. One sample was sacrificed for HPLC analysis at 24 hours, two at 48 hours, and three at 70 hours. The HPLC preparation consisted of stopping the reaction by addition of 50 µL of 40% $H_2SO_4$, centrifuging for 10 min at 1462×g, and filtering through a 0.45 µm filter. Samples were stored at 4° C.

HPLC analysis for ethanol
HPLC system—Agilent's 1100/1200 series with Chem station software
Degasser
Quaternary Pump
Auto-Sampler
Column Compartment /w Heater
Refractive Index Detector (RI)
Column—Bio-Rad HPX-87H Ion Exclusion Column 300 mm×7.8 mm parts #125-0140 Bio-Rad guard cartridge cation H parts #125-0129, Holder parts #125-0131
Method—0.005M $H_2OSO_4$ mobile phase
Flow rate of 0.6 ml/min
Column temperature—65° C.
RI detector temperature—55° C.

TABLE 5

| Relative ethanol yield. | |
|---|---|
| Enzyme | 70 h Ethanol |
| wt + Tc-AMG | 100% |
| PE085 + Tc-AMG | 100.55% |
| PE086 + Tc-AMG | 99.83% |
| PE096 + Tc-AMG | 100.15% |
| Tc-AMG only | 63.11% |

The results show that all of the tested variants according to the invention have retained their applicability in a raw starch hydrolysis process.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

The invention claimed is:

1. An alpha amylase variant, comprising a substitution at one or more positions corresponding to positions 128, 143, 141, 192, 20, 76, 123, 136, 142, 165, 219, 224, 265, 383, and 410 of the mature polypeptide of SEQ ID NO: 2, wherein the variant has alpha amylase activity, and wherein the variant alpha amylase has at least 90% sequence identity with the mature polypeptide of SEQ ID NO: 2.

2. The variant of claim 1, selected from the group consisting of:
   a) a polypeptide having at least 95% sequence identity to the mature polypeptide of SEQ ID NO: 2;
   b) a polypeptide encoded by a polynucleotide that hybridizes under high stringency conditions with (i) the mature polypeptide coding sequence of SEQ ID NO: 1, or (ii) the full-length complementary strand of (i);
   c) a polypeptide encoded by a polynucleotide with at least 95% identity with the mature polypeptide coding sequence of SEQ ID NO: 1; or
   d) a fragment of the mature polypeptide of SEQ ID NO: 2, which has alpha amylase activity.

3. The variant of claim 2, wherein the variant alpha amylase consists of the mature polypeptide of SEQ ID NO: 2 having a substitution, at one or more positions corresponding to positions 128, 143, 141, 192, 20, 76, 123, 136, 142, 165, 219, 224, 265, 383, and 410 of the mature polypeptide of SEQ ID NO: 2, and wherein the variant has alpha amylase activity.

4. The variant of claim 1, wherein the mature polypeptide of SEQ ID NO: 2 is the polypeptide of SEQ ID NO: 3.

5. The variant of claim 1, wherein the number of alterations is 1-20.

6. The variant according to claim 1, wherein the variant further comprises a linker and a carbohydrate binding module.

7. The variant of claim 1, which comprises one or more (several) substitutions selected from the group consisting of G20S, A76G, S123H, G128D, K136F, Y141W, Y141R, N142D, D143N, D165M, K192R, P219C, P224A, P224R, A265C, N383R, and V410A.

8. The variant of claim 7, wherein the variant comprises at least one of the following substitutions or combinations of substitutions:

D165M; or
Y141W; or
Y141R; or
K136F; or
K192R; or
P224A; or
P224R; or
S123H+Y141W; or
G20S+Y141W; or
A76G+Y141W; or
G128D+Y141W; or
G128D+D143N; or
P219C+Y141W; or
N142D+D143N; or
Y141W+K192R; or
Y141W+D143N; or
Y141W+N383R; or
Y141W+P219C+A265C; or
Y141W+N142D+D143N; or
Y141W+K192R V410A; or
G128D+Y141W+D143N; or
Y141W+D143N+P219C; or
Y141W+D143N+K192R; or
G128D+D143N+K192R; or
Y141W+D143N+K192R+P219C; or
G128D+Y141W+D143N+K192R; or
G128D+Y141W+D143N+K192R+P219C.

9. The variant according to claim 6, wherein the carbohydrate-binding module is a polypeptide comprising an amino acid sequence which has at least 90% identity with a sequence selected from the group consisting of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 and SEQ ID NO: 44.

10. The variant according to claim 9, wherein the linker has at least 90% sequence identity to SEQ ID NO:19 and carbohydrate-binding module has at least 90% sequence identity to SEQ ID NO: 36.

11. The variant according to claim 10, wherein the linker has at least 90% sequence identity to SEQ ID NO:21 and carbohydrate-binding module has at least 90% sequence identity to SEQ ID NO: 38.

12. A nucleic acid construct comprising the polynucleotide encoding the variant of claim 1.

13. An expression vector comprising the polynucleotide of claim 12.

14. A host cell comprising the polynucleotide of claim 13.

15. A method of producing a variant alpha amylase, comprising:
a) cultivating the host cell of claim 14 under conditions suitable for the expression of the variant; and
b) recovering the variant.

16. A method for producing a fermentation product from starch-containing material comprising the steps of:
(a) liquefying starch-containing material using a variant alpha-amylase according to claim 1;
(b) saccharifying the liquefied material obtained in step (a) using a glucoamylase; and
(c) fermenting the saccharified material using a fermenting organism.

17. A method for producing a fermentation product from starch-containing material comprising:
(a) saccharifying starch-containing material with a variant alpha amylase according to claim 1, and a glycoamylase at a temperature below the initial gelatinization temperature of said starch-containing material,
(b) fermenting using a fermenting organism.

18. The method according to claim 16, wherein the fermentation product is ethanol.

19. A method for producing an enzymatically modified starch derivative, comprising using a variant having alpha-amylase activity according to claim 1 for liquefying and/or saccharifying starch.

* * * * *